US007252959B2

(12) United States Patent  
Rand

(10) Patent No.: US 7,252,959 B2
(45) Date of Patent: Aug. 7, 2007

(54) ASSAYS FOR DIAGNOSIS OF THROMBOPHILIC DISEASE

(75) Inventor: Jacob H. Rand, New York, NY (US)

(73) Assignee: Mount Sinai School of Medicine of the City University of New York, New York, NY (US)

(*) Notice: Subject to any disclaimer, the term of this patent is extended or adjusted under 35 U.S.C. 154(b) by 0 days.

(21) Appl. No.: 11/028,339

(22) Filed: Jan. 3, 2005

(65) Prior Publication Data

US 2005/0208590 A1    Sep. 22, 2005

Related U.S. Application Data

(60) Continuation of application No. 09/796,023, filed on Feb. 28, 2001, now abandoned, which is a division of application No. 09/113,715, filed on Jul. 10, 1998, now Pat. No. 6,284,475.

(60) Provisional application No. 60/052,313, filed on Jul. 11, 1997.

(51) Int. Cl.
  *G01N 33/567* (2006.01)
  *G01N 33/86* (2006.01)
  *A61B 5/055* (2006.01)
(52) U.S. Cl. .................. 435/7.21; 435/7.92; 435/7.94; 435/13; 435/332; 436/63; 436/69; 424/9.34
(58) Field of Classification Search ............... 435/7.21, 435/7.92, 7.94, 13, 332; 436/63, 69; 424/9.34
See application file for complete search history.

(56) References Cited

U.S. PATENT DOCUMENTS

| 5,266,462 A | 11/1993 | Hemker et al. |
| 5,627,036 A | 5/1997 | Reutelingsperger |
| 5,632,986 A | 5/1997 | Tait et al. |
| 5,767,247 A | 6/1998 | Kaneko et al. |
| 5,955,437 A | 9/1999 | Reutelingsperger |
| 5,968,477 A | 10/1999 | Kasina et al. |

FOREIGN PATENT DOCUMENTS

| EP | WO 9603655 A1 | 2/1996 |
| FR | 2736197 | 1/1997 |

OTHER PUBLICATIONS

Casciola-Rosen et al. (Proceeding of the National Academy of Science, USA vol. 93, pp. 1624-1629, Feb. 1996, Immunology).*
Rauch, J. and Janoff, A.S., 1996, *Lupus* 5:498-502.
Sestier, K. et al., 1995, *C. R. Acad. Sci, Paris* 318:1141-1146.
Nakamura, N. et al., 1995, *American Journal of Hematology* 49:347-348.
Shapiro S.S., 1996, *Annu. Rev. Med.* 47:533.
Asherson R.A. et al. 1989, *Medicine* 68:366.
Rote et al., 1990, *Am. J. Obstet. Gynecol.* 163:575.
Yamamoto et al., 1990, *Clin. Exp. Immunol.* 94:196.
Triplett D.A., 1996 *Lupus* 5:431.
Giesen et al., 1991, *J. Biol. Chem.* 266:1379.
Krikun et al., 1994, *Placenta* 15:601.
Rand, J.H., 1998, *Am. J. Med. Sci.* 316:412.
Roubey 1994, *Blood* 84:2854.
Andree et al., 1992, *J. Biol. Chem.* 267:17907.
Tait et al., 1988, *Biochemistry* 27:6268.
Lockwood C.J., Rand J.H., 1994, *Obstet. Gyn. Survey* 49:432.
Lyden et al., 1992, *J. Reprod. Immunol.* 22:1.
Martin et al., 1995, *J. Exptl. Med.* 182:1545.
Sammaritano et al., 1992, *J. Clin. Immunol.* 12:27.
Ornstein et al., 1994, *J. Rheumatol.* 21:1360.
Yoshizaki, et al., 1989, *J. Biochem.* (Tokyo) 105:178.
Flaherty et al., 1990, *J. Lab. Clin. Med.* 115:174.
Andree et al. 1992, in Andree (ed.) *Phospholipid Binding and Anticoagulant Action of Annexin-V*, Maastricht, the Netherlands, Universitaire per Maastricht, p. 73.
Kohler et al., 1971, *J. Clin. Endocrin. Metals.* 32:683.
Messmore et al., 1994, *Semin. Thromb. Hemost.* 20:79.
Rand et al., 1994, *Am. J. Obstet. Gynecol.* 171:1566.
Jaffe et al., 1973, *J. Clin. Invest.* 52:2757.
Hinegardner, 1971, *Anal. Biochem.* 39:197.
Douglas and King, 1989, *J. Immunol. Meth.* 119:259.
Kliman et al. 1986, *Endocrinology* 118:1567.
Hajjar et al., 1996, *J. Biol. Chem.* 271:21652.
Sammaratino et al., 1990, *Semin. Arthritis Rheum.* 20:81.
Triplett, 1995, *Thromb. Haemost.* 74:329.
Huber et al., 1994, *In: The Annexins, Moss SE, ed.* London: Portland Press 105-124.
Branch et al., 1990, *Am. J. Obstet. Gynecol.* 163:210.
Blank and Tincani, 1994, *J. Autoimmun.* 74:441.
Krause et al., 1993, *Am. J. Reprod. Immunol.* 29:155.
Pierangeli and Harris, 1996, *Lupus* 5:451.
Tait et al., 1989, *J. Biol. Chem.* 264:7944.
Hasegawa et al., 1994, *Thromb. Res.* 74:77.
Smirnov et al., 1995, *J. Clin. Invest.* 95:309.
Vogt and Rote, 1997, *Am. J. Obstet and Gynecol.* 177:964.
Rand et al.,1997, *Am. J. Obstet Gynecol.* 177:918.
Rand et al., 1997, *N. Engl. J. Med.* 337:154.
Thiagarajan et al., 1990, *J. Biol. Chem.* 265:17420.
Lockshin M.D., 1996, *Lupus* 5:404.
Conley C.L., Hartmann R.C., 1952, *J. Clin. Invest.* 31:621.
Dachary-Prigent, 1993, *Blood*, vol. 81, No. 10, pp. 2554-2565.
Bevers et al., 2000, *Thromb. Haemostas.* vol. 83, No. 5, pp. 792-794.
Willems et al., 2000, *Biochemistry*, vol. 39, 1982-1989.

* cited by examiner

*Primary Examiner*—Long V. Le
*Assistant Examiner*—Lisa V. Cook
(74) *Attorney, Agent, or Firm*—Baker Botts L.L.P.

(57) ABSTRACT

The present invention provides methods for diagnosing and/or monitoring thrombophilic disease in a patient that can result from the antiphospholipid antibody syndrome (aPL syndrome). The methods of the invention are premised on the inhibition of binding of an anticoagulant protein, annexin, preferably annexin-V, to phospholipids by antiphospholipid (aPL) antibodies in a patient blood sample.

9 Claims, 15 Drawing Sheets

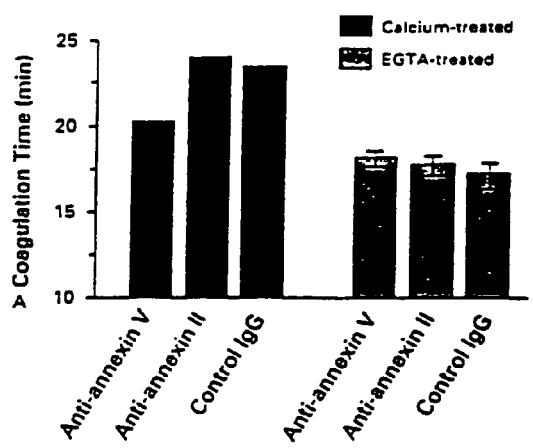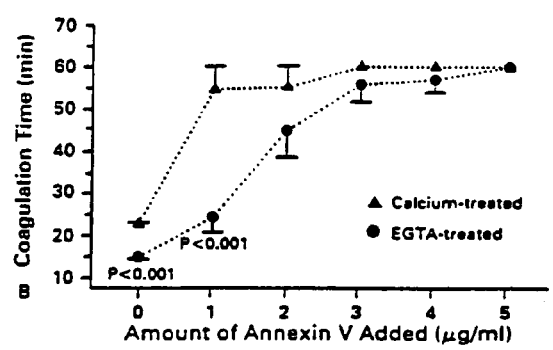
FIGURE 3

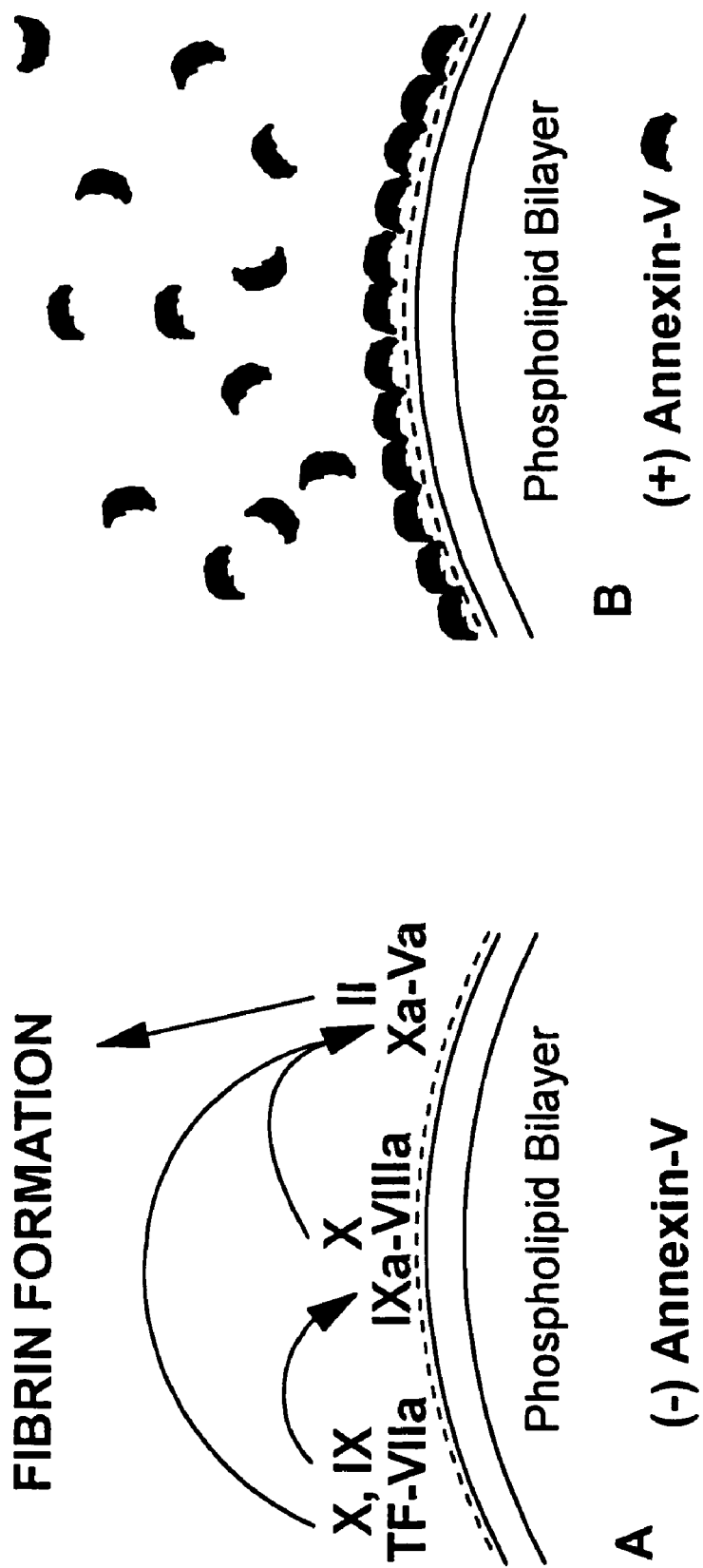
FIGURE 4A & B

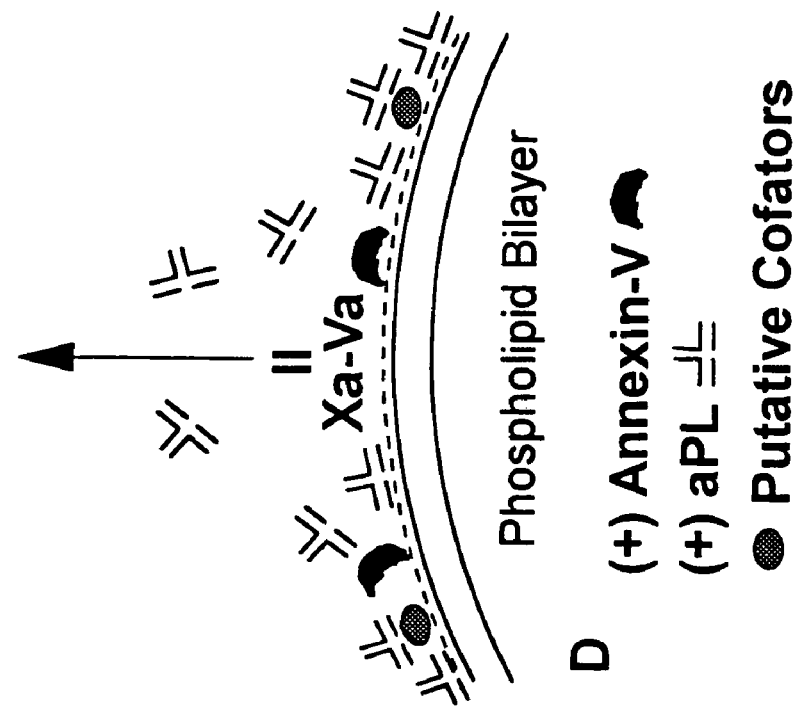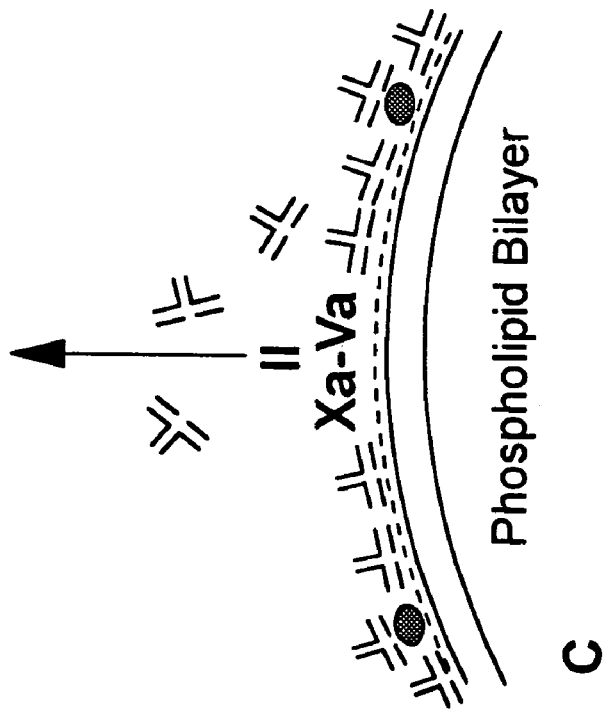
FIGURE 4C & D

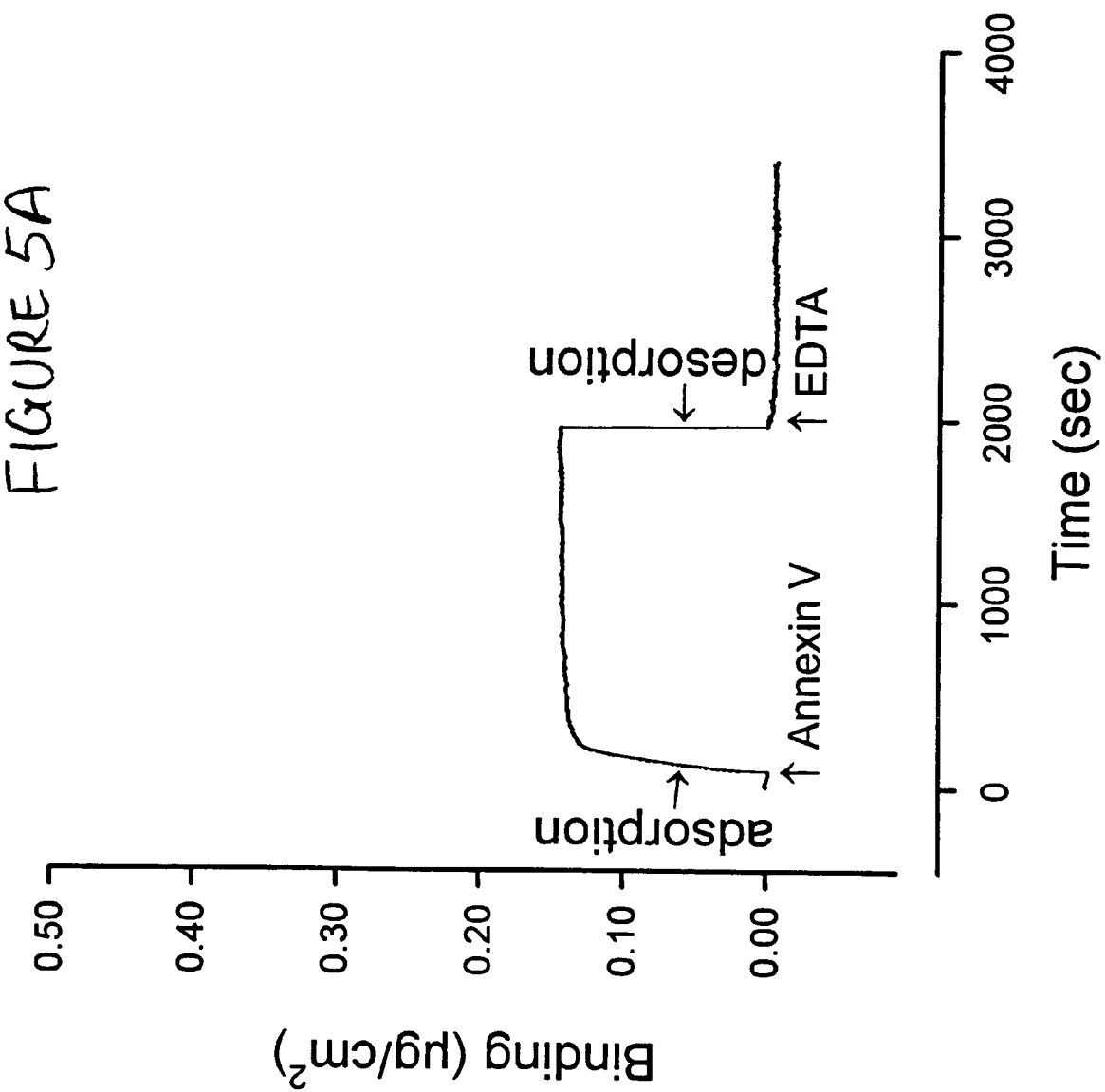

ASSAYS FOR DIAGNOSIS OF THROMBOPHILIC DISEASE

CROSS-REFERENCE TO RELATED APPLICATIONS

The present application is a continuation of U.S. application Ser. No. 09/796,023, filed Feb. 28, 2001 now abandoned, which is a divisional of U.S. application Ser. No. 09/113,715, filed Jul. 10, 1998, now U.S. Pat. No. 6,284,475, which claims priority to U.S. Provisional Application No. 60/052,313, filed Jul. 11, 1997, all the disclosures of which are specifically incorporated herein by reference.

The invention disclosed herein was carried out with grants from the U.S. government. The U.S. has certain rights to the invention.

BACKGROUND OF THE INVENTION

The present invention is directed to assays for detection of a thrombophilic disease in a patient. The assays, which are based on the diagnosis of the antiphospholipid antibody syndrome (aPL syndrome) in an individual, detect the capacity of a patient sample to inhibit the binding of annexin-V, an anticoagulant protein, to a phospholipid substrate, and thereby block the anticoagulant activity of annexin-V.

The presence of antibodies in blood which recognize anionic phospholipids, or anionic phospholipid protein complexes, has been associated with a thrombophilic syndrome known as the antiphospholipid (aPL) antibody syndrome. The aPL syndrome, which is also known as the lupus anticoagulant syndrome, or the anticardiolipin antibody syndrome, is characterized by arterial and venous thrombosis or, by recurrent pregnancy loss attributed to placental thrombosis (Lockwood C. J., Rand J. H., 1994, *Obstet. Gyn. Survey* 49:432; Lockshin M. D., 1996, *Lupus* 5:404; Shapiro S. S., 1996, *Annu. Rev. Med.* 47:533; Asherson R. A, Khamashta M. A., Ordi Ros J., Derksen R. H. W. M., Machin S. J., Barquinero J., Outt H. H., Harris E. N., Vilardell-Torres M., Hughes G. R. V., 1989, *Medicine* 8:366). The aPL syndrome thus comprises a thrombophilic disease distinguished by antibodies that recognize anionic phospholipid complexes. The disorder may occur spontaneously or in conjunction with another autoimmune disorder such as systemic lupus erythematosus (Conley C. L., Hartmann R. C., 1952, *J. Clin. Invest.* 31:621), hence the name "lupus anticoagulant."

Paradoxically, aPL syndrome antibodies appear to manifest as "lupus anticoagulants" (Conley et al. 1952, *J. Clin. Invest.* 31:621; Shapiro S. S., 1996, *Annu. Rev. Med.* 47:533; Triplett D. A., 1996 *Lupus* 5:43) in vitro by inhibiting phospholipid-dependent blood coagulation. Yet, in vivo, these "anticoagulants" are associated with thrombotic mechanisms, and rarely, if ever, with any bleeding disorders.

Evidence has been accumulating that the aPL syndrome bears relationship to the presence of anticoagulant proteins found on the surface of endothelial cells that come into contact with blood. Such anticoagulant proteins include a family of proteins known as annexins, a principal member being annexin-V. Annexin-V, which is also known as placental anticoagulant protein-1 or vascular anticoagulant-α, has potent anticoagulant properties in vitro that are based on its high affinity for anionic phospholipids and its capacity to displace coagulation factors from phospholipid bilayers (Andree et al., 1992, in Andree (ed.) *Maastricht, the Netherland,* Universitaire pers Maastricht, p. 73). Annexin-V, which is normally present on the apical surface of placental syncytiotrophoblasts, has been found to be reduced on apical membranes of placental villi from aPL syndrome patients (Krikun et al., 1994, *Placenta* 15:601; Sammaritano et al., 1992, *J. Clin. Immunol.* 12:27).

The aPL syndrome has been shown to be an important risk factor for stroke, equivalent in predictive value to hypertension (Rand, J H, 1998, *Am. J. Med. Sci.* (In press)). Moreover, aPL antibodies are associated with recurrent arterial and venous thrombosis. Approximately 40% of patients on hemodialysis have aPL antibodies, which may be associated with graft thrombosis (the problem of graft thrombosis alone has an estimated cost in the United States of $700 million/year, which is equal to the cost of hemodialysis). aPL antibodies have also been associated with recurrent pregnancy loss, however, current diagnostic methods have not proven specific enough to allow for treatment before a woman has experienced at least three spontaneous abortions. Currently, it is recommended that patients diagnosed for aPL antibodies with thrombosis receive high intensity anticoagulant therapy for the remainder of their lives. Thus there is a need for developement of specific assays for diagnosis and monitoring of thrombophilic disease in susceptible individuals, i.e., those known to have aPL syndrome or at risk for aPL syndrome.

Such methods can be useful for screening for risk of stroke, recurrent miscarriages and risk of thrombosis or embolism, as well as evaluating for the etiology of patients presenting with the above disorders, all of which may be classified as thrombophilic diseases. In addition, there has been an increasingly frequent clinical problem in the identification of patients with incidental positive antiphospholipid antibody tests (7-10% of the general population, and up to 40% of ill hospital patients) with no accepted means to distinguish abnormalities that are clinically relevant (disease related) from those that are irrelevant. The present invention is directed to providing specific assays to be used as a basis for making those distinctions.

The methods of the present invention are based upon the interaction of phospholipid substrates, aPL antibodies and annexin-V and, also, the consequent coagulant activity of the complex exposed to clotting factors. The methods can be used to diagnose thrombophilic disease (or hypercoaguable disease) in susceptible individuals (i.e., those having or at risk of developing aPL syndrome) by utilizing the reduction in binding of annexins, particularly annexin-V, to phospholipid substrates in the presence of a blood specimen from a known or suspected aPL syndrome patient as a marker of the disease. The present invention thus provides for specific assays which are predictive of and can monitor thrombophilic disease, as well as the success of treatment.

SUMMARY OF THE INVENTION

The present invention provides methods for diagnosing and/or monitoring thrombophilic disease in a patient that can result from the antiphospholipid antibody syndrome (aPL syndrome). The methods of the invention are premised on the inhibition of binding of an anticoagulant protein, annexin, preferably annexin-V, to phospholipids by antiphospholipid (aPL) antibodies in a patient blood sample.

in one aspect, the method involves incubating a phospholipid substrate with a test blood specimen (plasma, serum, isolated IgG) in the presence of a known amount of an annexin, preferably annexin-V, for a time sufficient to allow the annexin to bind to the phospholipid substrate. The unbound annexin and specimen are removed from the substrate and the amount of annexin bound to the substrate in the presence of the test specimen is measured and compared to an amount of annexin bound in the presence of a control specimen (known to not contain aPL antibodies), wherein a lower amount of annexin bound in the presence of the test specimen versus the control indicates the presence of thrombophilic disease in the individual.

In a variation of the above method, the amount of unbound annexin is measured, wherein a higher amount of unbound annexin in the test specimen compared to the control indicates thrombophilic disease in the patient.

In a further aspect of the invention, the method involves diagnosing and/or monitoring thrombophilic disease in a patient using a coagulation assay. The latter methods are premised on the anticoagulant effect of annexin (annexin-V), which effect is reduced or inhibited by aPL antibodies. The coagulation assay may be carried out as a one or two stage assay.

In a one stage assay, anticoagulated patient plasma is incubated in duplicate with a phospholipid dependent coagulation test reagent, followed by calcifying the plasma to induce clotting. In one of the duplicate samples, annexin is added and in the other, annexin is not present. The time to clot formation in both samples, wherein a reduced anticoagulant effect in the presence of annexin indicates thrombophilic disease.

In a two stage assay, anticoagulated patient plasma, serum or IgG is incubated in duplicate with the coagulation test reagent. The patient sample is removed and the duplicate reagents are incubated further with a sample of control plasma, preferably pooled normal plasma. The samples are then calcified in the presence and absence of annexin, as above, and monitored for time to clot formation. Again, a reduced anticoagulation effect in the presence of annexin indicates thrombophilic disease.

DESCRIPTION OF THE DRAWINGS

FIG. 1A shows that the mean (±SE) level of annexin V, indicated by the horizontal line and error bar, was significantly lower after exposure to antiphospholipid IgG than after exposure to control IgG (0.37±0.02 vs. 0.85±0.12 ng per well, P=0.02).

FIG. 1B shows how antiphospholipid IgG affects annexin-V levels on primary cultured trophoblasts and BeWo trophoblasts. (The data on the former were normalized for the DNA concentration, and both sets of data were normalized as percentages of the control values so that the two cell types could be shown together.) Annexin-V levels on the surface of both types of trophoblasts were significantly reduced (P<0.001 for both).

FIG. 1C shows the coagulation time of plasma added to BeWo trophoblasts exposed to preparations of IgG from the three patients for two hours at 4° C., as compared with controls. In these experiments, annexin-V was not dissociated from the cells. The mean (±SE) coagulation time was significantly shorter in the antiphospholipid-IgG-exposed trophoblasts than in the controls (8.7±2.0 vs. 21.3±2.9 minutes, P=0.02).

FIG. 2A shows that the mean (±SE) level of annexin V, indicated by the horizontal line and error bar, was significantly lower after exposure to antiphospholipid IgG than after exposure to control IgG (1.6±0.04 vs. 2.1±0.05 ng per well, P=0.001).

FIG. 2B shows the coagulation time of plasma added to these cultures of endothelial cells. Overall, the mean (±SE) coagulation time was significantly shorter in the three groups of antiphospholipid-antibody-exposed endothelial cells than in the controls (9.8±0.8 vs. 14±21.2 minutes, P=0.04).

FIG. 2C shows the annexin-V levels after endothelial cells were cultured with preparations of antiphospholipid IgG from the three patients and control IgG for 20 hours at 37° C., a temperature at which recycling of membranes and vesicles occurs. The mean (±SE) level of annexin-V in the cells exposed to antiphospholipid IgG was significantly lower than the level in the control cells (1.3±0.2 vs. 2.1±0.1 ng per well, P=0.02).

FIG. 2D shows the coagulation time of plasma added to endothelial cells cultured with IgG preparations from the three patients and the controls for 20 hours at 37° C. Again, the coagulation time was significantly shorter for the endothelial cells exposed to antiphospholipid antibody, with a lower mean value in those cells than in the control cells (17.2±0.2 vs. 23.5±1.2 minutes, P=0.006).

FIGS. 3A-B. Effects of Polyclonal Antiannexin Antibodies and Purified Annexin-V on the Coagulation of Plasma Exposed to Umbilical-Vein Endothelial Cells.

FIG. 3A shows that the mean (±SE) coagulation time of plasma was significantly less after cells were incubated with rabbit poly-clonal anti-annexin-V as compared with equal concentrations of control rabbit polyclonal IgG (20.1±0.6 vs. 23.8±0.5 minutes, P=0.006). Treatment with rabbit polyclonal anti-annexin II had no effect (coagulation time, 23.8±0.8). When cells were pretreated with EGTA, which dissociates cell-surface annexin V, there was no difference between the results obtained with the various antibodies.

FIG. 3B shows how dissociating and restoring annexin-V affects the coagulation of plasma exposed to umbilical-vein endothelial cells. The plasma coagulation time was significantly shorter after annexin-V was dissociated from the cell surface by treatment with EGTA alone as compared with calcium (mean of eight experiments, 14.6±0.9 vs. 22.5±0.5 minutes; P<0.001). When exoge-nous annexin-V was added to the culture, dose-dependent prolongations of plasma coagulation were observed. The difference in the coagulation time between cells treated with EGTA and those treated with calcium was also significant when 1 μg of annexin-V was added per milliliter (P<0.001).

FIGS. 4A-D. Model for mechanisms of the "lupus anticoagulant effect" and the inhibition of annexin-V and acceleration of coagulation by antiphospholipid antibodies.

FIG. 4A. Anionic phospholipids (negative charges), when exposed on the apical surface of the cell membrane bilayer, serve as potent cofactors for the assembly of three different coagulation complexes: the tissue factor (TF)-VIIa complex, the IXa-VIIIa complex and the Xa-IXa complex, and thereby accelerating blood coagulation. The TF complexes yield either factor Va or factor Xa, the IXa complex yields factor Xa (prothrombinase), and the Xa formed from both of these reactions is the active enzyme in the prothrombinase complex which yields factor IIa (thrombin), which in turn cleaves fibrinogen to form fibrin.

FIG. 4B Annexin-V, in the absence of aPL antibodies, forms clusters which bind with high affinity to the anionic phospholipid surface and shield the surface from the assembly of the phospholipid-dependent coagulation complexes, thereby inhibiting coagulation reactions.

FIG. 4C In the absence of annexin-V, aPL antibodies can prolong the coagulation times, compared to control antibodies, by reducing the access of coagulation factors to anionic phospholipids. This may result in a "lupus anticoagulant" effect.

FIG. 4D However, in the presence of annexin-V, antiphospholipid antibodies, either directly or via interactior with protein-phospholipid cofactors, disrupt the the ability of annexin-V to cluster on the phospholipid surface, resulting in a net increase of the amount of anionic phospholipid to available for promoting coagulation reactions. This manifests in the net acceleration of coagulation in vitro and in thrombophilia in vivo.

FIGS. 5A-D. Ellipsometry studies of effects of aPL IgG and cofactor on displacement of annexin-V from PS/PC phospholipid bilayers.

FIG. 5A shows the rapid adsorption of annexin-V to the PS/PC (30%/70%) phosphoilpid bilayer. Treatment with ethylenediaminetetraacetic acid (EDTA) and measurement of the desorption of this protein can be used to measure the amount of annexin-V on the phospholipid surface. As shown, this calcium-dependent binding protein is completely desorbed from the phospholipid surface by addition of 6 mM EDTA, FIG. 5B shows that incubation of the annexin-V coated phospholipid bilayer with a polyclonal human aPL IgG in the absence of $\beta_2$-glycoprotein I does not displace the annexin-V—i.e. the quantity of annexin-V desorbed after treatment With EDTA matches the quantity of annexin-V which had originally adsorbed, FIG. 5C shows incubation of the annexin-V coated phospholipid bilayer with $\beta_2$-GP I followed by polyclonal aPL IgG results in a significant reduction of the quantity of annexin-V on the bilayer. This is reflected by the marked reduction of the amount of annexin-V which desorbs after treatment with EDTA.

FIG. 5D shows treatment of the phospholipid bilayer with the $\beta_2$-GP I cofactor followed by a control (non-aPL) IgG) fraction does not change the quantity of annexin-V on the phospholipid surface at all—i.e., the quantity of annexin-V which is desorbed by treatment with EDTA is the same as the quantity which had been adsorbed in the first place.

FIG. 8A. Washed human platelets were exposed to 3 different aPL and control IgG preparations in plasma, following which the platelets were incubated with annexin-V (20 μg/ml), in the presence of calcium, as described in Methods. Surface annexin-V was then dissociated with EGTA and measured by ELISA. Platelets pre-exposed to aPL IgG had significantly less annexin-V on their surfaces (mean±SEM-0.89±0.12 $ng/10^6$ platelets) as compared to controls (2.01±0.38 $ng/10^6$ platelets, p=0.05).

FIG. 8B. Plasma coagulation times were determined using platelets which had been pre-exposed to the aPL and control IgGs in plasma. The platelets were added to pooled normal plasma which was recalcified in the presence and absence of added annexin-V (20 μg/ml). Annexin-V lengthened the coagulation times of pooled normal plasma with both control and aPL IgG-treated platelets. However, the net prolongation, compared to the coagulation time without annexin-V, was significantly less with the aPL-treated platelets (mean prolongation±SEM: 33.2±0.9 sec) as compared to controls (50.4±4.1 sec, n=3, p=0.01).

FIG. 9A. aPTT reagent-phospholipid was exposed to 4 different aPL and control plasmas and then to annexin-V (2 μg/ml), after which surface annexin-V was dissociated with EDTA and measured by ELISA. aPTT reagent--phospholipid which had been pre-exposed to aPL-plasmas had significantly less annexin-V (mean±SEM: 318±28 ng/50 μl aliquot of reagent) as compared to controls (656±80 ng/50 μl aliquot of reagent, p=0.01).

FIG. 9B. Plasma coagulation times were determined using aPTT reagent-phospholipid exposed to the aPL and control plasmas (n=10 for each group) in the first stage and then in the second stage, to pooled normal plasma in the presence and absence of added annexin-V (30 μg/ml). Annexin-V delayed the coagulation times of aPTT reagent exposed to both types of plasmas. In the presence of annexin-V, the coagulation times of the aPTT reagent which had been pre-exposed to aPL-plasma was significantly faster (mean±SEM: 89.2+9.2 sec) than reagent exposed to the control plasma (1 02.5±2.6 sec, p=0.001). Also, there was a significant decrease in the net prolongation of the coagulation times induced by annexin-V (mean±SEM: 1 3.6±1.8 see for aPL plasmas versus 23.1±0.8 sec for controls, p=0.0002).

FIG. 10A. Prothrombin time reagent was pre-exposed to 3 different aPL and control IgG preparations in plasma and then to annexin-V (2 μg/ml), after which surface annexin-V was dissociated with EDTA and measured by ELISA. Prothrombin time reagent pre-exposed to aPL IgG-containing plasmas had significantly less annexin-V (mean±SEM-82±4 ng/50 μl aliquot of reagent) compared to controls (110±1 ng/50 μl aliquot of reagent, p=0.002).

FIG. 10B. Plasma coagulation times were determined using prothrombin time reagent which was exposed to the aPL and control plasmas (n=10 for each group) in the first stage and, in the second stage, to pooled normal plasma in the presence and absence of annexin-V (30 μg/ml). There was a small but significant prolongation of coagulation time when the prothrombin time reagent was exposed to the aPL plasmas in the absence of annexin-V (p=0.003). Addition of annexin-V resulted in prolongation of coagulation times with both types of reagent (i.e. exposure to control and aPL plasmas). However, in contrast to the results without annexin-V, the coagulation times of the prothrombin time reagent which had been pre-exposed to aPL -plasma were significantly shortened (mean±SEM: 35.0±0.8 sec compared to 38.3±1.2 sec for control plasmas, p=0.03). There was a concomitant significant decrease in the net prolongation of the coagulation times using PT reagent which had been pretreated with aPL plasma (10.3±0.8 sec compared to 15.2±1.2 sec for control plasmas, p=0.004).

DETAILED DESCRIPTION OF THE INVENTION

Figure 1:
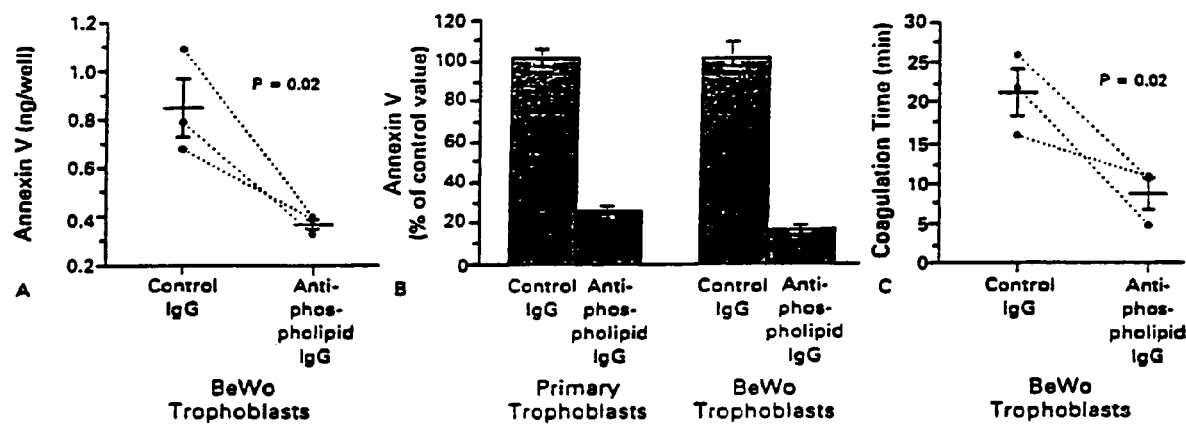
FIGS. 1A-C. Effects of Antiphospholipid-Antibody IgG on Annexin-V and Plasma Coagulation on Trophoblasts. Cultured trophoblasts (from the BeWo cell line) grown to confluence were exposed to IgG preparations (2 mg per milliliter) from three patients and their controls for two hours at 4° C. to inhibit the recycling of membranes and vesicles. Annexin-V was then dissociated with buffer containing ethylene glycol-bis(β-aminoethyl ether) N,N,N',N'-tetraacetic acid (EGTA) and measured by immunoassay. (All tests were performed in quadruplicate.)

The present invention is directed to methods of detecting and/or diagnosing thrombophilic disease in an individual that can result from the antiphospholipid antibody syndrome (aPL syndrome). The methods of the invention involve measuring the inhibition of annexin-V binding to anionic phospholipid substrates by antiphospholipid (aPL) antibodies in a patient blood sample. The methods are particularly useful in diagnosing and/or monitoring thrombophilic disease in susceptible individuals, i.e., those known to have or be at risk for the aPL syndrome. Such individuals undergo accelerated coagulation of their blood compared to normal individuals, and are at increased risk to suffer arterial and/or venous thrombosis and spontaneous pregnancy losses (i.e. miscarriages). The increased risk of stroke, recurrent miscarriages, and risk of thrombosis or embolisms correlated with the aPL syndrome may all be classified as thrombophilic (or hypercoagulable) diseases.

The present invention is premised on the finding, disclosed herein, of a new thrombogenic mechanism in the aPL syndrome—that IgG fractions from aPL patients reduce the quantity of annexin-V on cultured trophoblasts and endothelial cells and accelerate the coagulation of plasma added to these cells. In addition, the present invention also provides that this effect also occurs with other phospholipid substrates, such as phospholipid-coated surfaces, frozen thawed washed platelets and phospholipid suspensions used for conventional clinical coagulation tests. Thus, the phospholipid substrates useful in the present invention can include, inter alia, cultured trophoblasts, endothelial cells (particularly human umbilical vein endothelial cells—HUVECs), other cells and cell lines that display surface anionic phospholipids, platelets, phospholipid coated silicon wafers, phospholipid coated microtiter plates, phospholipid coated beads, phospholipid suspensions and clinical coagulation test reagents comprising phospholipids. The phospholipids include, inter alia, phosphatidyl serine, phosphatidyl choline, phosphatidyl ethanolamine, phosphatidyl inositol, cardiolipin, phosphatidic acid and combinations thereof. Preferred phospholipids include phosphatidyl serine, phosphatidyl choline and combinations thereof.

In accordance with the invention, ellipsometry studies have provided direct evidence that aPL IgG preparations, in the presence of a cofactor, e.g., $\beta_2$-glycoprotein I ($\beta_2$-GP I), displace annexin-V from phosphotidyl serine/phosphatidyl choline (PS/PC) phospholipid bilayers. $\beta_2$-GP I is a serum factor that appears to be required for aPL antibody binding to phospholipids (Roubey 1994, *Blood* 84:2854, incorporated herein by reference). In addition, other proteins, such as prothrombin, may also serve as cofactors. In accordance with the invention, when aPL IgG is used in practice, both the aPL IgG and $\beta_2$-GP I are believed necessary for annexin displacement to occur. $\beta_2$-GP I is not required to be added if aPL plasma or serum is used. It has also been found that incubating PS-coated microliter plate wells with aPL patient plasmas results in the significant reduction of the quantity of labeled annexin-V which binds to this phospholipid substrate.

In addition, exposing phospholipid substrates used for coagulation reactions, such as washed frozen thawed platelet suspensions, partial thromboplastin time (aPTT) reagent and prothrombin time (PT) reagent, to aPL antibodies reduces the quantity of annexin which binds to these phospholipid substrates. Using cell cultures, platelets and non-cellular phospholipid substrates, the aPL antibodies also accelerate coagulation in the presence of anticoagulant proteins, such as annexin, reducing the potent anticoagulant activity of this phospholipid-binding protein.

The novel findings underlying the invention, which demonstrate accelerated coagulation by aPL antibodies when annexin-V is present in coagulation reactions, stand in contrast to the "lupus anticoagulant" phenomenon which was first described in 1952 (Conley, 1952, *J. Clin. Invest.* 31:621). The present invention provides the first direct demonstrations of the displacement of annexin-V and the acceleration of coagulation on noncellular phospholipid substrates by aPL antibodies and provide a methodology suitable for clinical testing for thrombophilic disease. While the invention exemplifies the use of annexin-V in the methods for testing for thrombophilic disease, other members of the annexin family (Tait et al., 1988, *Biochemistry* 27:6268, incorporated herein by reference), as well as other phospholipid-binding anticoagulant proteins, are encompassed within the scope of the invention. Since annexin-V has the highest affinity for phospholipid among the various members of the annexin family, it is believed that aPL antibodies will have a similar effect on displacing lower affinity annexins, e.g. annexin-II, which might also have antithrombotic properties (Hajjar et al., 1996, *J. Biol. Chem.* 271:21652, incorporated herein by reference) from phospholipid substrates.

Since, in accordance with the invention, aPL antibodies are capable of reducing the binding of annexin-V to anionic phospholipids in vitro and in cell culture, it is believed that this effect also occurs in vivo where anionic phospholipids are exposed to flowing blood. Such situations and processes include the surface of placental villi (Lyden et al., 1992, *J. Reprod. Immunol.* 22:1), activated platelets (Thiagarajan et al., 1990, *J. Biol. Chem.* 265:17420), apoptic cells and cellular particles (Martin et al., 1995, *J. Exptl. Med.* 182: 1545) and disrupted erythrocyte membranes. In all of these settings, the presence of aPL antibodies could inhibit the binding of circulating anticoagulants, such as annexin-V, which, in turn, results in a membrane surface which is more thrombogenic.

Thus, according to the invention, aPL antibodies have a prothrombic effect on phospholipid substrates in vivo and in vitro. The mechanism by which aPL antibodies accelerate coagulation in the presence of annexin-V is believed to be due to topographical differences between the binding of the two ligands (aPL antibodies and annexin) to phospholipid substrates. Annexin-V binds in clusters on the phospholipid surface while aPL antibodies disrupt this carpet of annexin-V, which normally would shield the surface and allow enough room on the phospholipid surface for coagulation factors such as prothrombin to bind. Thus, the prothrombotic effect of the aPL antibodies is believed to be due to their increasing the net quantity of available anionic phospholipid for coagulation reactions by displacing annexin-V from the surface. In view of the present findings, it is believed that the afore mentioned paradoxical "lupus anticoagulant" phenomenon is a reflection of the effects of the aPL antibodies in the presence of coagulation proteins in plasma, but in the absence of annexin-V; in this situation the antibodies will prolong coagulation by decreasing the net quantity of phospholipids available for coagulation reactions (since annexin-V is not present). In reflecting the relative inhibitory effects of high affinity antiphospholipid-protein complexes—in the absence of annexin-V—to the binding of coagulation factors, the invention also provides that the "lupus anticoagulant" phenomenon may indeed serve as a surrogate marker for antibodies whose actual pathophysiogic function lies in their capacity to displace annexin-V.

In accordance with the present invention, FIG. 4 depicts a model underlying the basis for the methods provided herein. Anionic phospholipids on the apical surfaces of cell membranes serve as the cofactor for coagulation complex, which accelerate blood clotting (FIG. 4A). Annexin-V is believed to play a physiologic role in inhibiting blood coagulation reactions on vascular surfaces (phospholipids substrates) by shielding highly thrombogenic anionic phospholipids from coagulation enzyme complexes (FIG. 4B). It is believed that aPL syndrome patients have antibodies with a sufficient affinity for anionic phospholipids (and/or presumptive cofactors, such as $\beta_2$-GP I) to disrupt or prevent the assembly of this annexin-V protective shield. This results in a net increase of exposed phospholipid and permits a more procoagulant topography to be available for coagulation reactions. Thus, coagulation systems which include annexin-V will demonstrate a relative acceleration of coagulation—a "lupus procoagulant effect"—due to displacement of annexin-V by aPL syndrome antibodies (FIG. 4D). In contrast, in the absence of added annexin-V, only the relatively inhibitory effects of the antibodies on phospholipid-dependent coagulation reactions are observed (as compared to when antibodies are absent), thereby resulting in the classical "lupus anticoagulant" effect (FIG. 4C).

With reference to FIG. 4A, according to the present invention, it has now been shown that the binding of annexin-V to the phospholipid substrate inhibits prothrombinase (factor Xa) activity, thereby inhibiting the formation of thrombin. Annexin-V normally displaces prothrombinase (and also other phospholipid dependent complexes) from the phospholipid substrate, thus inhibiting prothrombinase activity. aPL antibodies (isolated IgG and cofactor) interferes with the annexin displacement of prothrombinase, thereby promoting clotting.

Thus, in one embodiment of the invention, a method for diagnosing and/or monitoring thrombophilic disease in a patient (i.e., a patient with or suspect of having the aPL syndrome) is provided in which the amount of annexin bound to a phospholipid substrate in the presence of a blood specimen from a patient suspected of having thrombophilic disease related to the aPL syndrome is compared to a reference amount of annexin bound to a companion phospholipid substrate in the presence of a control blood specimen. The control blood specimen may be obtained from a single source or, preferably, may be derived from a pool of normal donors. The latter provides a reference range that minimizes variations possible with individual samples. Such pools can be characterized and standardized for repeated use in the assays. They are aliquoted and stored frozen for use, providing a ready source of standardized control specimens. Following an incubation period, unbound annexin and blood specimens are removed and the amount of annexin bound to the phospholipid substrate is measured. The amounts bound in the presence or absence of test sample are compared. A lower amount of bound annexin from the test specimen indicates the presence of aPL antibodies in the specimen and the likelihood that the individual has thrombophilic disease related to the aPL syndrome.

The test and control samples can be whole blood, plasma, serum and isolated IgGs. Plasma is preferred to whole blood, but the plasma must be anticoagulated for use in the binding assays. Preferably, the anticoagulated plasma is citrated, however, other anticoagulants known to those of skill in the art, including EDTA, heparin, and hirudin are also useful. Likewise, serum and, more preferably, isolated IgG can be used. IgG can be isolated from blood samples by any IgG isolation procedure known to those of skill in the art.

When isolated IgGs are used in the assay, the addition of a cofactor, such as $\beta_2$-glycoprotein I, which enhances aPL antibody binding to phospholipids, is preferred. Other cofactors that can be used include prothrombin. A cofactor is not required when plasma or serum is used.

Annexins used in the invention can be isolated by known techniques from placenta or can be synthesized by recombinant DNA techniques known to those of skill in the art. In a preferred embodiment, the annexin is annexin-V isolated from placenta or obtained by recombinant techniques.

As used in the invention, the annexins can optionally comprise a detectable label which allows for measurement of annexin in the assays. Such labels include, inter alia, biotin, radioisotopes, such as $^{125}$I and $^{131}$I, fluorochromes, such as fluorescein isothiocyanate (FITC), chromophores and any other such labels, such as chemiluminescent labels, known to those of skill in the art. The use of such labels allows for the design of specific assays, such as radioimmunoassays using monoclonal or polyclonal antibodies that specifically interact with the annexin, especially annexin-V, direct fluorescence or chemiluminescence measurements compared to a standard protein curve, and the use of streptavidin binding to biotin to specifically measure biotin labeled annexin.

Alternatively, unlabeled annexin, particularly annexin-V, can be detected and quantitated by means of enzyme-linked immunoassays (ELISA), as is well known in the art, utilizing monoclonal or polyclonal antibodies, specific for annexins, particularly annexin-V.

Measurement of the amount of annexin bound to the phospholipid substrate can be performed in situ, i.e., on the substrate, or on annexin removed from the phospholipid substrate, e.g., by desorbing with a calcium chelator such as EDTA or EGTA. The afore mentioned measurement assays can all be performed in situ or on desorbed annexin.

The phospholipid substrates for use in the invention include, inter alia, trophoblasts, such as primary trophoblasts or cultured trophoblast cell lines, e.g., BeWo; endothelial cells, preferably human umbilical vein endothelial cells (HUVECs); other cells and cell lines having surface anionic phospholipids; frozen thawed washed platelets; phospholipid suspensions; phospholipid coated silicon wafers; phospholipid coated microtiter plates; phospholipid coated beads and phospholipid dependent clinical coagulation test reagents, such as partial thromboplastin time (aPTT), prothrombin (PT) reagents and other phospholipid dependent coagulation tests known to those of skill in the art. The advantages of the coagulation tests, such as aPTT and PT reagents, and platelets are that they can also be used in further coagulation measurements as described below.

Phospholipids for use in the invention are known to those in the art and include, inter alia, phosphatidyl serine, phosphatidyl choline, phosphatidyl ethanolamine, phosphatidyl inositol, cardiolipin, phosphatidic acid and combinations thereof. Preferred phospholipids include phosphatidyl serine, phosphatidyl choline and combinations thereof.

In another embodiment of the present invention, a similar approach is taken where the annexin is bound to the phospholipid substrate in the presence or absence of a test blood specimen as described above. However, instead of measuring the amount of annexin bound to the phospholipid substrate, the amount of annexin remaining in the supernatant is measured, as described above. In this embodiment, a higher amount of annexin, detected and measured as described above in the supernatant of test samples compared to controls indicates the presence of aPL antibodies in the sample which is correlated with thrombophilic disease in the patient.

In a further embodiment of the invention, the methods for detecting an/or monitoring thrombophilic disease utilize measuring coagulation of plasma in the presence of annexin on phospholipid substrates to detect the functional consequences of the reduction of annexin, preferably annexin-V, by aPL antibodies in a patient sample. The patient sample is preferably anticoagulated plasma, i.e., plasma in which a known anticoagulant is present, or, in some cases, IgG. Citrated plasma is preferably used, although other anticoagulants known in the art, such as EDTA, heparin and hirudin, can be used as well. For such assays, the phospholipid substrate comprises a phospholipid dependent coagulant test, preferably aPTT or PT reagent or, alternatively, frozen thawed washed platelets. In such assays, the tests are performed in the presence and absence of annexin in order to measure the anticoagulant effect of the protein.

Coagulation assays may be a single stage or two state assay. For single stage assays, useful for screening a number of patients, anticoagulated plasma from a patient is incubated with a phospholipid-dependent coagulation test, such as aPTT or PT reagent. The plasma is then recalcified (e.g., using calcium ions, such as $CaCl_2$, to counteract the effects of the anticoagulant) in the presence and absence of a known reference amount of annexin (annexin-V) that provides a standardized anticoagulant effect, incubated and the time to clot formation is monitored. In a one stage assay, the patient plasma provides both aPL antibodies and the coagulation factors necessary for clothing. Parallel assays may optionally be carried out with control plasma. A reduced anticoagulant effect seen with the patient plasma in the presence of annexin indicates thrombolytic disease in the patient.

The coagulation assay may also be carried out as a two stage assay, which is preferred for monitoring individual patients because of greater consistency of the assay. In the two stage assay, anticoagulated plasma, serum or IgG, from a patient is incubated with the coagulation test reagent, as above. The patient sample is removed and anticoagulated pooled normal plasma is added to the test reagent. The latter plasma is then recalcified, as above, in the presence and absence of a reference amount of annexin and the time to clot formation monitored. The use of the pooled plasma in the second stage minimize the variable baseline coagulation times of individuals.

In practice of the two stage assay, an aPTT or PT reagent is incubated with either anticoagulated patient plasma (or IgG) or control plasma (or IgG), followed by sedimenting the mixture, removing the unbound plasma (or IgG) and resuspending the reagent. Anticoagulated pooled normal plasma is added and, following a brief incubation, a calcium ion solution (e.g. $CaCl_2$) with and without annexin (preferably annexin-V) is added to the samples, whereafter the time to clot formation is monitored.

As above, for the single stage, if aPL antibodies are present in the patient plasma, significantly accelerated coagulation times and reductions of the anticoagulant effects of the annexin will be observed when compared to control plasma, indicating thrombophilic disease in the patient. The reduced anticoagulant effects of the annexin is manifest in patient samples when plasma containing annexin is compared with plasma lacking annexin.

In a still further aspect of the present invention, the methods disclosed herein may be useful in detecting low affinity mutant or polymorphic annexins in patients. Thus, the methods are useful for detecting annexin in patients that have functional defects such as decreased anticoagulant and antithrombotic properties.

As disclosed, the present invention provides methods for detecting the ability of aPL antibodies in patient plasma to displace annexins from phospholipid substrates. Functionally defective polymorphic or mutant annexins may also be measured in these assays.

Polymorphic annexins may be isolated by affinity chromatography using monoclonal or polyclonal antibodies specific to various annexins, e.g., annexin-V. The binding of such annexins to phospholipid substrates in the presence of aPL antibodies can be measured as above. Mutant annexins with decreased binding are believed to be associated with hypercoagulability, which those with increased binding are believed to be associated with hypocoagulability (bleeding disorders).

Likewise, the effects of mutant annexins can be measured in the coagulation assays described herein, using the PT and aPTT reagents. Mutant annexins having decreased anticoagulant effectiveness are associated with hypercoagulability, while those with increased anticoagulant effectiveness are associated with hypocoagulability.

Finally in a specific aspect of this embodiment, the effects of purified monoclonal aPL antibodies having low and high affinities on mutant annexin binding to phospholipid substrates and their anticoagulant effectiveness can be measured. Mutant annexins having decreased anticoagulant effectiveness are expected to be inhibited by low affinity aPL antibodies and be associated with hypercoagulability. On the other hand, mutant annexins having increased anticoagulant effectiveness are expected to resist inhibition by high affinity aPL antibodies and be associated with hypocoagulability (i.e., bleeding disorders).

EXAMPLE 1

Isolation of IgG

IgG antibodies were isolated from the citrated plasma of three patients with severe antiphospholipid (aPL)-antibody syndrome and three normal control subjects using a protein G column, as described by Sammaritano et al., 1992, *J. Clin. Immunol.* 12:27, incorporated herein by reference. A preparation of antiphospholipid antibody from each of the three patients was studied and compared with a preparation from one of the controls. The three patients all had severe primary aPL-antibody syndrome, that is, there was no evidence of systemic lupus erythematosus or any other autoimmune disorder, and high titers of anticardiolipin IgG.

The first patient was a 33-year old woman (previously described by Ornstein et al., 1994, *J. Rheumatol.* 21:1360, incorporated herein by reference) who had evidence of a previous cerebral infarct on a computed tomographic scan, previous cerebral infarct on a computed tomographic scan, previous deep-vein thrombosis and pulmonary embolism, and four consecutive losses of pregnancy. She presented with a fifth pregnancy loss at 18 weeks' gestation, placental infarction, and infarcts on the skin of her hands and face, with fibrin thrombi in the small vessels of the dermis. The second patient was a 47 year-old man with catastrophic antiphospholipid syndrome, manifested by deep-vein thrombosis, pulmonary emboli, and stroke. The third patient was a 63-year-old woman with stroke, pulmonary embolism, and infarcts on the skin of her hands.

EXAMPLE 2

Plasmas

For studies with plasmas, citrated specimens were collected from 10 patients with aPL syndrome and 10 non-aPL controls at the Mount Sinai Medical Center, New York, N.Y. The IgGs and plasmas were tested for the presence of antibodies against $\beta_2$-GP I, prothrombin and annexin-V with standardized nitrocellulose (Schleicher & Schueli, Keene, N. H.) dot-blots containing varying quantities of the proteins, up to 1 μg. All 3 of the purified aPL IgGs recognized $\beta_2$-GP I directly, one of the 3 recognized purified human prothrombin, and none recognized annexin-V directly. Of the 10 aPL plasmas, nine contained immunoglobulin which recognized $\beta_2$-GP I, one recognized prothrombin alone, and none recognized annexin-V directly. To provide the same standard plasma for the second stage of coagulation tests, plasmas from three normal blood bank donors were pooled, alliquotted and stored at –40° C. for all coagulation studies.

EXAMPLE 3

Annexin-V

Annexin-V was purified from human placentas as described by Yoshizaki, et al., 1989, *J. Biochem.* (Tokyo) 105:178, incorporated herein by reference. The identity of the protein was confirmed by immunoblot analysis using a previously characterized affinity purified monospecific polyclonal rabbit anti-annexin-V IgG (Krikun et al., 1994, *Placenta* 15:601, incorporated herein by reference). For studies of annexin-V binding to phosphatidyl serine-coated microtiter plates (described below), the protein was labeled with biotin as previously described (Flaherty et al., 1990, *J. Lab. Clin. Med.* 115:174, incorporated herein by reference). Annexin-V was dialyzed at 4° C. against buffer containing 0.05 M boric acid, 0.1 M NaCl, pH 8.5. Biotin-NHS (Calbiochem-Novabiochem Corporation, La Jolla, Calif.) was then added to the annexin-V at a 1:2 molar ratio of annexin-V to biotin-NHS. The reaction was carried out for 30 min at 4° C. and quenched with 10 mM glycine. The biotinylated annexin-V was then dialyzed against TBS buffer (0.05M Tris, OAM NaCl, pH 7.4). The concentration of biotinylated annexin-V was determined by absorbance at 280 nM and aliquots were stored at –70° C.

EXAMPLE 4

Effects of IgG on Trophoblast Annexin-V

A human trophoblast cell line (BeWo), obtained from the American Type Culture Collection (Rockville, Md.), was maintained as described (Kohler et al., 1971, *J. Clin. Endocrin. Metals.* 32:683; Messmore et al., 1994, *Semin. Thromb. Hemost.* 20:79, both incorporated herein by reference). The BeWo cells were resuspended in a basal medium composed of a 1:1 mixture of phenol red-free Ham's F12 and Dulbecco's modified Eagle's medium plus 10 percent fetal-calf serum. They were then plated at densities of 60,000 cells per well in 96-well culture plates and grown to confluence (approximately 130,000 cells per well). Either aPL-antibody IgG or control IgG (2 mg per milliliter) in basal medium plus 10 percent fetal-calf serum was added, and the cells were incubated for two hours at 4° C. to inhibit the recycling of membranes and vesicles. The cells were then washed once in HEPES buffer (pH 7.4) containing 5 mM calcium chloride, followed by a wash in HEPES buffer containing 1 mM ethylene glycol-bis(β-amioethyl ether)-N,N,N',N'-tetraacetic acid (EGTA) in place of calcium, to dissociate cell-surface annexin-V. Levels of annexin-V were determined by an enzyme-linked immunosorbent assay (ELISA) (Rand et al., 1994, *Am. J. Obstet. Gynecol.* 171:1566; Flaherty et al., 1990, *J. Lab. Clin. Med.* 115:174, both incorporated herein by reference) that used a previously characterized, affinity-purified, monospecific, polyclonal rabbit anti-annexin V IgG antibody (Krikun et al., 1994, *Placenta* 15:601, incorporated herein by reference). In assays in which known quantities of purified annexin-V were added, the presence of aPL or control IgG did not in itself reduce the levels of annexin-V. All the studies were performed with quadruplicate culture wells. Trypan-blue exclusion studies showed that the treated cells were at least 95 percent viable.

EXAMPLE 5

Experiments with Cultured Primary Trophoblasts

To determine whether the effects observed with the BeWo trophoblast cell line also occurred with primary cultured trophoblasts (cytotrophoblasts), the latter were obtained from women undergoing elective cesarean sections at term. The cells were isolated by a modification of the procedure of Douglas and King (*J. Immunol. Meth.* 119:259, 1989, incorporated herein by reference) in which anti-CD45 antibodies conjugated to magnetic microspheres (Advanced Magnetics, Cambridge, Mass.) were substituted for the anti-HLA antibodies used in the original procedure (Kliman et al. 1986, *Endocrinology* 118:1567, incorporated herein by reference)

The cells were washed, resuspended in basal medium supplemented with 2 percent charcoal-stripped calf serum and culture supplement (ITS+, Collaborative Biomedical Products, Bedford, Mass.), and seeded in 96-well culture plates at a density of 100,000 cells per well. The cultures were maintained at 37° C. in a humidified atmosphere containing 5 percent carbon dioxide and 95 percent air, and the medium was changed at 48 hours.

The cells were allowed to form syncytia for 72 hours before the IgG was added, which was done in the manner described in Example 4 for the trophoblast cell line. The final wash, with HEPES buffer containing 1 mM EGTA, was assayed for annexin-V by ELISA as described in Example 4. Since cultured primary trophoblasts do not proliferate, the results of these experiments were normalized for the DNA concentrations, which were determined by fluorimetry on the cells after their detachment, as described by Hinegardner 1971, *Anal. Biochem.* 39:197, incorporated herein by reference. All these experiments were performed with quadruplicate culture cells.

EXAMPLE 6

Experiments with Cultured Umbilical-Vein Endothelial Cells

Human umbilical-vein endothelial cells (HUVECs) were harvested and cultured as previously described by Jaffe et al., 1973, *J. Clin. Invest.* 52:2757, incorporated herein by reference). They were plated at a density of 20,000 cells per well in 96-well culture plates, allowed to grow to confluence (approximately 140,000 cells per well), and treated in the same way as the BeWo trophoblasts. In addition to the short-term cultures at 4° C., the HUVECs were also cultured with the IgG fractions at 37° C. for 20 hours, after which the cells were washed once in HEPES buffer containing 5 mM calcium chloride and then washed in HEPES buffer containing 1 mM EGTA in place of calcium, to dissociate cell-surface annexin-V. The levels of annexin-V were determined by an ELISA as described above (Example 4). In addition, for coagulation studies with plasma, parallel cultures of HUVECs were incubated with the IgG fractions at 37° C. for 20 hours, washed once in HEPES buffer containing 5 mM calcium chloride, and then tested as described in the following section. Quadruplicate culture wells were used in all the studies.

EXAMPLE 7

Studies of Coagulation

After the cells were grown to confluence in the 96-well tissue-culture microtiter plates, studies of coagulation were performed as follows: the cells were first washed three times in HEPES buffer containing 5 mM calcium chloride and then incubated with either antiphospholipid or control IgG (5 mg per milliliter) in basal medium plus 10 percent fetal-calf serum for 90 minutes at 4° C. After a washing in HEPES buffer, the cells were overlaid with normal pooled plasma (100 μl per well) recalcified with 11 μl of 70 mM calcium chloride in the case of the BeWo cells. It was necessary to add the same volume (11 μl) of 200 mM calcium chloride in order to observe coagulation of plasma in the case of the HUVECs. Quadruplicate culture wells were used in all the studies.

The culture plates were then placed in a kinetic microtiter-plate reader, and the formation of fibrin was observed as an increase in the optical density to 0.100 at a wavelength of 405 nm. It was confirmed that this assay indeed monitors the formation of fibrin by determining that adding porcine intestinal-mucosa heparin (0.5 U per milliliter) (Steris Laboratories, Phoenix, Ariz.) or recombinant hirudin (0.5 μg per milliliter) (kindly provided by Ciba-Geigy, Summit, N.J.) to the plasma completely inhibited any change in optical density. Furthermore, in the absence of heparin or hirudin the formation of fibrin nets could be observed with the unaided eye.

In order to determine whether reducing cell-surface annexin V without aPL antibodies might affect the coagulation of plasma, experiments were performed in which HUVECs that were not incubated with human IgG fractions were washed in HEPES buffer containing 5 mM calcium chloride and EGTA, to preserve or dissociate surface annexin-V. The HUVECs were then incubated with rabbit polyclonal anti-annexin-V IgG antibodies (100 μg per milliliter) for 90 minutes at 4° C., after which they were overlaid with recalcified plasma and the time to coagulation measured. The controls included equivalent concentrations of polyclonal rabbit anti-annexin-II IgG (kindly provided by Dr. Katherine Hajjar, Cornell University Medical College) and a polyclonal rabbit antimouse idiotype IgG (kindly provided by Dr. Thomas Moran, Mount Sinai School of Medicine, New York, N.Y.).

In addition, HUVECs washed three times in HEPES buffer that contained 5 mM. calcium chloride, to preserve cell-surface annexin-V, were compared with cells that were washed three times in HEPES buffer containing 1 mM EGTA, to dissociate cell-surface annexin-V. Each of these treatments was followed by a washing in buffer containing calcium chloride, after which the cells were overlaid with recalcified normal pooled plasma containing various concentrations of annexin-V; the HUVECs were then monitored for coagulation as described above. In addition, the coagulation times of the HUVECs incubated with plasma containing recombinant annexi-II at a concentration of 4 μg per millileter (kindly provided by Dr. Hajjar) were compared with those of cells incubated with plasma containing annexin-V in the same concentration and cells incubated with HEPES-buffer control.

Statistical Analysis

All the statistical analyses herein were performed with the use of Student's two-tailed t-test (InStat program, Graphpad, San Diego, Calif.).

EXAMPLE 8

Effects of Antiphospholipid Antibodies on Annexin-V and Plasma Coagulation in Trophoblasts The effects of aPL IgG on levels of annexin-V associated with the trophoblast cell surface, using the BeWo trophoblast cell line (Example 4) was studied. With each of the three different aPL IgG antibodies (Example 1), the amount of annexin-V associated with the trophoblast cell surface was significantly lower than that associated with control IgG, and the reductions were similar (FIGS. 1A and 1B). It was then determined whether these reductions also occurred with primary cultured placental trophoblasts (cytotrophoblasts) (Example 5). When these trophoblasts were incubated with aPL IgG, there was a significantly lower amount of annexin-V, approximately 20 percent of the amount found in trophoblasts incubated with control IgG (FIG. 1B).

It was then tested whether the reduction in the amount of the annexin-V anticoagulant protein was associated with a shortening in the coagulation time of a plasma exposed to these cells. There was indeed a significant shortening in the clotting times of plasma on the trophoblasts exposed to antiphospholipid IgG, as compared with those exposed to control IgG (FIG. 1C).

EXAMPLE 9

Figure 2:
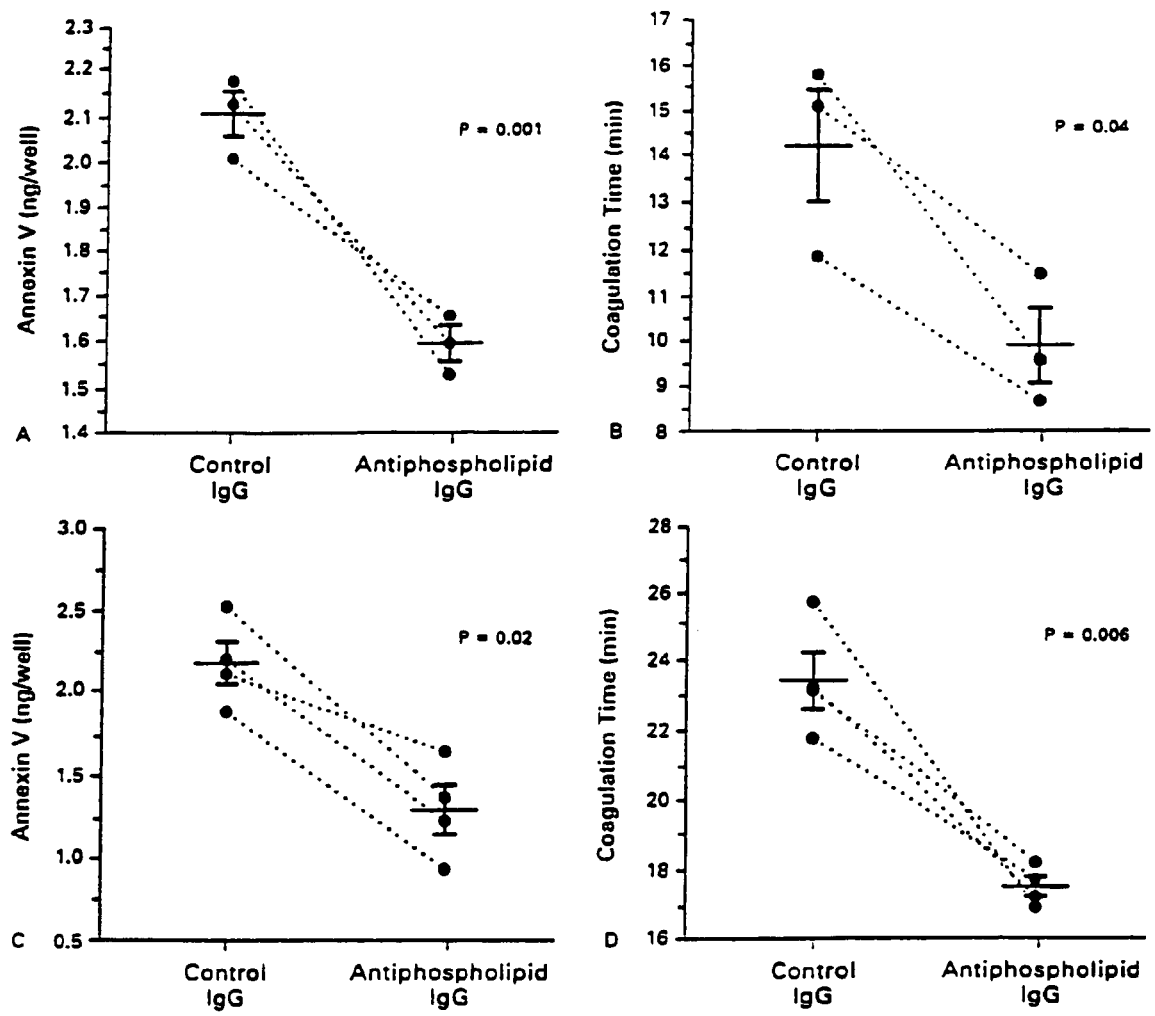
FIG. 2A-D. Effects of Antiphospholipid-Antibody IgG on Annexin-V and Plasma Coagulation on Umbilical-Vein Endothelial Cells. Umbilical-vein endothelial cells were exposed to IgG preparations from three patients and their controls for two hours at 4° C. to inhibit the recycling of membranes and vesicles.

Effects of Antiphospholipid Antibodies on Annexin-V and Plasma Coagulation in Umbilical-Vein Endothelial Cells The aPL-antibody syndrome may lead to thrombosis in veins and arteries. In view of the findings with trophoblasts (Example 8), the effects of aPL antibodies on levels of annexin-V and plasma coagulation on the surfaces of HUVECs. As was found with trophoblasts (Example 8), levels of annexin-V were reduced on the surface of epithelial cells exposed to antiphospholipid antibody (FIG. 2A). There was also a significant acceleration of coagulation on the surface of HUVECs exposed to aPL IgG as compared with control IgG (FIG. 2B). The results were similar with HUVECs cultured at 37° C. for 20 hours with the antibodies (FIGS. 2C and 2D).

When HUVECs not treated with aPL IgG were incubated with rabbit polyclonal anti-annexin-V IgG, the coagulation time of plasma applied to the cells was significantly shorter than after incubation with antimouse IgG, and treating the HUVECs with anti-annexin II IgG had no effect on the coagulation time (FIG. 3A). This shorter coagulation time did not occur with cells from which the annexin-V was first dissociated with EGTA (FIG. 3A). Also, removing annexin-V from the endothelial surface by preincubation with EGTA significantly reduced the coagulation time (FIGS. 3A and 3B). Furthermore, adding exogenous annexin-V resulted in dose-dependent prolongations of coagulation in both cells whose annexin-V had been removed by EGTA treatment and controls whose annexin-V had been preserved by treatment with calcium-containing buffer (FIG. 3B). In contrast, there was no difference in the mean (±SE) coagulation time between the epithelial cells exposed to plasma containing 4 µg of annexin II pre milliliter and the controls exposed to buffer alone (19.5±0.6 vs. 19.8±0.2 minutes).

EXAMPLE 10

Ellipsometry Studies

The effects of aPL antibodies on phospholipid-bound annexin-V were studied using computer-assisted ellipsometry (Andree et al. 1992, in Andree (ed.) *Phopholipid Binding and Anticoagulant Action of Annexin-V*, Maastricht, the Netherlands, Universitaire per Maastricht, p. 73, incorporated herein by reference). Planar phospholipid bilayers were applied to silicon slides as previously described. (Andree et al., 1992, *J. Biol. Chem.* 267:17907; Giesen et al., 1991, *J. Biol. Chem.* 266:1379, both incorporated herein by reference.) A 5 mM vesicle mixture of 30% 1,2-dioleoyl-sn-glycero-3-phosphatidyl serine and 70% 1,2-dioleoyl-sn-glycero-3-phosphatidyl choline (PS/PC) (Avanti Polar-Lipids, INC. Alabaster, Ala.) was dried under nitrogen and sonicated (Sonic Dismembrator model F60, Fisher Scientific, Pittsburgh, Pa.) in HEPES buffer (0.01 M HEPES, 0.14 M NaCl, pH 7.5) at 0° C. until the suspension was completely clear. Silicon slides of 1 by 4 cm and 0.4 mm thickness were cut from silicon wafers (Wacker Chemie, Munich, Germany, n-type, phosphor-doped). The slides were thoroughly cleaned with detergent (Sparkleen, Fisher Scientific Company, Pittsburgh, Pa.) and water. Then they were kept overnight in 30% chromic sulfuric acid, flushed with water and stored in 50% alcohol-water until use, when they were rinsed with distilled water and then dipped into a container containing stirring HEPES buffer composed of 0.01 M HEPES, 0.14 M NaCl, 0.1% BSA, 5 mM $CaCl_2$, pH 7.5. The sonicated PS/PC vesicles (final concentration 50 µM) were then added and stirred for 10 min. Each slide was flushed with the latter HEPES buffer and transferred to an ellipsometer cuvette containing the stirring buffer. Adsorption of annexin-V (2 µg/ml), $\beta_2$-glycoprotein I($\beta_2$-GP I) (2 µg/ml, provided by Dr. K. McCrae, Temple University) and IgG preparations (100 µg/ml) to the phospholipid bilayers on the silicon slide were observed after the serial addition of each of the proteins. The mass of the PS/PC bilayer (~0.4 µg/cm$^2$) was measured and subtracted for these curves. After adsorption had reached equilibrium, residual annexin-V was desorbed from the phospholipid bilayers on the silicon slide by the addition of 0.5 M EDTA (to a final concentration of 6 mM) and measured. Addition of EDTA had no effect upon the adsorptions of IgGs or $\beta_2$-GP I-, alone or in combination. The completeness of desorption of annexin-V from the surface by EDTA was further confirmed by subsequently solubilizing the phospholipid bilayers with 0.1% SDS. The SDS solubilized samples were checked for annexin-V by standard immunoblot with a monospecific polyclonal rabbit anti-annexin-V IgG following 0.1% SDS-12% polyacrylamide gel electrophoresis as described in Krikun et al., 1994, *Placenta* 15:601, incorporated herein by reference.

EXAMPLE 11

Annexin-V Binding to Phosphatidyl Serine-Coated Microtiter Plates

Microtiter plates (Nunc-Immuno Plate, MaxiSorp Surface) (Fisher Scientific, Pittsburgh, Pa.) were coated with phosphatidyl serine PS (Avanti Polar-Lipids, INC. Alabaster, Ala.) as previously described (Yamamoto et al., 1990, *Clin. Exp. Immunol.* 94:196; Rote et al., 1990, *Am J. Obste.t Gynecol.* 163:575, both incorporated herein by reference,) and used as the phospholipid substrate. Citrated plasma samples (50 µl) were added to each well in duplicate and incubated for 30 minutes at room temperature. The wells were emptied and washed 4× with PBS buffer, pH 7.4. 50 µl of biotinyiated-annexin-V (1 µg/ml in TBS buffer containing 0.1% BSA and 5 mM $CaCl_2$, pH 7.4) was then added to each well and incubated for 30 minutes at room temperature. The wells were washed 4× with PBS buffer, followed by 50 µl of phosphatase-labeled streptavidin (0.5 µg/ml in TBS buffer containing 0.1% BSA) (Kirkegaard & Perry, Laboratories, Gaithersburg, Md.), which was incubated for 30 minutes at room temperature. The wells were then emptied and washed 4× with PBS buffer, pH 7.4. 50 µl of p-nitrophenyl phosphate substrate (1 mg/ml in DEA buffer) (Sigma Chemical Company, St. Louis, Mo.) were added and incubated for approximately 30 minutes at room temperature, after which the optical absorbance was read at 405 nm with a kinetic microplate reader (Molecular Devices, Menlo Park, Calif.).

EXAMPLE 12

Annexin-V Binding/Desorption Assays and Coagulation Studies with Washed Platelets Platelets were prepared for coagulation studies according to the method previously described for the platelet aPTT test ("platelet neutralization procedure") (Thiagarajan et al., 1990, *J. Biol. Chem.* 265:17420, incorporated herein by reference). Pooled platelets from blood bank donors were washed 3× in TBS buffer (0.15 M NaCl, 0.02 M Tris) containing 1 mg/ml glucose, pH 7.4, resuspended to a density of $2 \times 10^5/\mu l$ in the buffer, aliquotted and stored at −70° C. for all studies.

The effects of aPL IgGs on the quantity of platelet-associated annexin-V bound by platelets were performed with modified methods similar to those described above for cultured trophoblasts and endothelial cells. (Examples 4 and 6). aPL and control IgGs were added to normal citrated plasma to a final concentration of 5 mg/ml. Aliquots of frozen and thawed washed platelets ($1 \times 10^8$) were incubated with 100 µl of the plasmas at 4° C. for 2 hrs, as described above. The platelets were washed 3× and resuspended in HEPES buffer containing 5 mM $CaCl_2$, pH 7.4. Annexin-V was then added to the platelets in the HEPES buffer containing 5 mM $CaCl_2$ to a final concentration of 20 µg/ml (determined after pilot studies with varying concentrations of annexin-V) and incubated at 4° C. for an additional 15 minutes. The platelets were then centrifuged and washed 3× in the same buffer. After the final centrifugation, to dissociate annexin-V, the platelets were resuspended in the HEPES buffer containing 1 mM EGTA. The quantity of platelet associated annexin-V was determined by an ELISA (as described in Examples 4 and 6). The results of the assays were expressed as ng of annexin-V/$10^6$ platelets.

The effects of aPL IgG on coagulation using platelets exposed to aPL or control IgGs were also studied. For these experiments the IgGs were added to pooled normal plasma to a concentration of 5 µg/ml. Thawed washed platelets (120 µl), at a density of $2 \times 10^5/\mu l$ in the TBS buffer described above, were added to 120 µl of IgG-containing plasma and pre-incubated for 10 min at 37° C. The platelets were centrifuged, washed 2× and resuspended in 120 µl of the TBS buffer. A 50 µl volume of the platelet suspension was then added to 50 µl of pooled normal plasma, incubated for 30 sec at 37° C. in a ST4 Coagulation Instrument (American Bioproducts Co. Parsipanny, N.J.). 50 µl of Celite (5 g/L in TBS buffer consisting of 0.05 M Tris, 0.1 M NaCl, pH 7.4) was added and the mixture was incubated for 60 sec. A volume of 50 µl of 0.02 M $CaCl_2$, or 0.02 M $CaCl_2$ containing annexin-V at 20 µg/ml was then added, the times until clot formation were measured and the mean times of duplicate tests were reported. Coagulation times of specimens without and with annexin-V were recorded, along with the net prolongations (i.e. coagulation time in the presence of annexin-V minus coagulation time in the absence of annexin-V) which reflected the anticoagulant activity of the annexin-V.

EXAMPLE 13

Annexin-V Binding/Desorption Assays and Coagulaton Studies with aPTT Reagent The effects of aPL IgG on the quantity of annexin-V associated with a partial thromboplastin time (aPTT) reagent-phospholipid (Actin FS) (Baxter Diagnostics Inc., Deerfield, Ill.) was studied. 100 µl of the aPTT phospholipid-reagent was incubated with 100 µl of aPL patient plasma or control plasma for 15 minutes at 37° C. The mixture of aPTT reagent-phospholipid and plasma was sedimented with a microcentrifuge (Model 5451, Brinkmann Instruments, Inc, Westbury, N.Y.) at 15,000×g for 20 minutes at room temperature. The plasma treated-phospholipid pellets were washed 3× with HEPES buffer (0.01 M HEPES, 0.14 M NaCl, 0.1% BSA, pH 7.4) and resuspended in HEPES buffer containing 5 mM $CaCl_2$. Annexin-V was then added into the phospholipid suspension to a final concentration of 2 µg/ml and incubated at 37° C. for 10 minutes. After centrifugation, the phospholipid pellets were washed 3× in HEPES buffer containing 5 mM $CaCl_2$. The phospholipid-associated annexin-V was then dissociated from the aPTT phospholipid-reagent with HEPES buffer containing 5 mM EDTA and assayed by ELISA as described above. The results of the assays were expressed as ng of annexin-V/50 µl aliquot of aPTT phospholipid-reagent.

The effect of aPL IgG on coagulation with aPTT reagent-phospholipid was determined using a 2 stage assay, in which the first stage exposed aPTTs reagent-phospholipid to potential aPL antibodies in the test plasma, and the second stage measured coagulation times with the phospholipid using a pooled normal plasma. This assay was designed using the pooled normal plasma for the second stage in order to deal with the variable baseline coagulation times of individual patients. 50 µl of the aPTT reagent-phospholipid was added to 50 µl of aPL patient or control citrated plasma. The mixture was sedimented with the microcentrifuge, as described above. The pellets were then washed once in the TBS buffer and resuspended in 220 µl of this buffer. 50 µl of this plasma treated phospholipid suspension was added to 50 µl pooled normal plasma and incubated for 120 sec at 37° C. in the ST4 Coagulation Instrument, after which 50 µl of 0.02 M $CaCl_2$ or 0.02 M $CaCl_2$ containing annexin-V (30 µg/ml) was added. The times until clot formation of duplicate specimens were monitored and reported, as described above for platelets (Example 12).

EXAMPLE 14

Annexin-V Binding/Desorption Assays and Coagulation Studies with Prothrombin Time Reagent The effect of aPL IgG on the quantity of annexin-V associated with prothrombin time (PT) reagent (tissue factor) was studied. PT reagent (Thromboplastin-C Plus, Baxter Diagnostics Inc, Deerfield, Ill.) was washed 3× with TBS buffer by sedimentaion and resuspension with the microcentrifuge for 20 minutes at 15,000×g, as described for the aPTT phospholipid-reagent (Example 13). 100 µl of the washed phospholipid of PT reagent was incubated with 100 µl of aPL or control IgG-containing plasma (at a concentration of 5 mg/ml, prepared as for the platelets described above in Example 12) for 15 minutes at 37° C. The mixture was then centrifuged and the pellets of IgG-treated PT reagent-phospholipid were then treated in the same way as described above for aPTT reagent-phospholipid (Example 13). The phospholipid-associated annexin-V was dissociated from the PT phospholipid-reagent by the HEPES buffer containing 5 mM EDTA the and was assayed by ELISA, as described above. The results were reported as described for the aPTT reagent embodiment of this method, above.

In order to investigate the effects of aPL IgG on coagulation with PT reagent, a two-stage assay, similar to the aPTT assay described above (Example 13), was used. The PT reagent (50 µl) was washed 3× in TBS buffer to remove calcium, and was added to 50 µl of aPL patient or control plasma. The mixtures were centrifuged as described above and the pellets were washed once in the TBS buffer and resuspended in 220 μl of this buffer. 50 μl of the suspension was then added to 50 μl pooled normal plasma and incubated for 120 sec at 37° C. in the ST4 Coagulation Instrument. A 50 μl volume of 0.02 M CaCl$_2$ or 0.02 M CaCl$_2$ containing annexin-V (30 μg/ml) was added. The times until clot formation of duplicate specimens were monitored and recorded as described above.

EXAMPLE 15

Fluorometric Determination of Annexin-V Binding to Phospholipid

The effect of aPL plasma on the binding of fluorescein isothiocyanate (FITC)-conjugated annexin-V to phospholipid was also determined. 50 μl of aPTT phospholipid-reagent was added to 50 μl of aPL or control plasma and sedimented in the microcentrifuge as described above. The pellets of plasma treated-phospholipid were washed once in the TBS buffer, pH 7.4, and then resuspended in 55 μl of the above buffer containing 5 mM CaCl$_2$ and 1 μg/ml of FITC-conjugated annexin-V (Clontech Laboratories, Inc. Palo Alto, Calif.). The mixture was incubated for 5 minutes at room temperature and centrifuged as described above, after which the supernatants were collected and the pellets were resuspended in 55 μl of the TBS buffer containing 10 mM EDTA. The levels of labeled annexin-V in the supernatant and bound to the aPTT phospholipid-reagent were measured in terms of relative fluorescence intensity with an SLM/Amico SPF-500C spectrofluorometer (Milton Co. Rochester, N.Y.). The samples were contained in 50 μl quartz microcuvettes, thermostated at 20° C. Excitation was at 490 nm with a 4-nm band-pass and emission was detected at 523 nm with a 20-nm band-pass. The results were reported as relative fluorescence units (RFU). A standard curve of fluorescence intensity versus FITC-annexin-V concentration was linear between 0 and 2 μg/ml of protein.

EXAMPLE 16

Results of Ellipsometry Studies

Figure 5B:
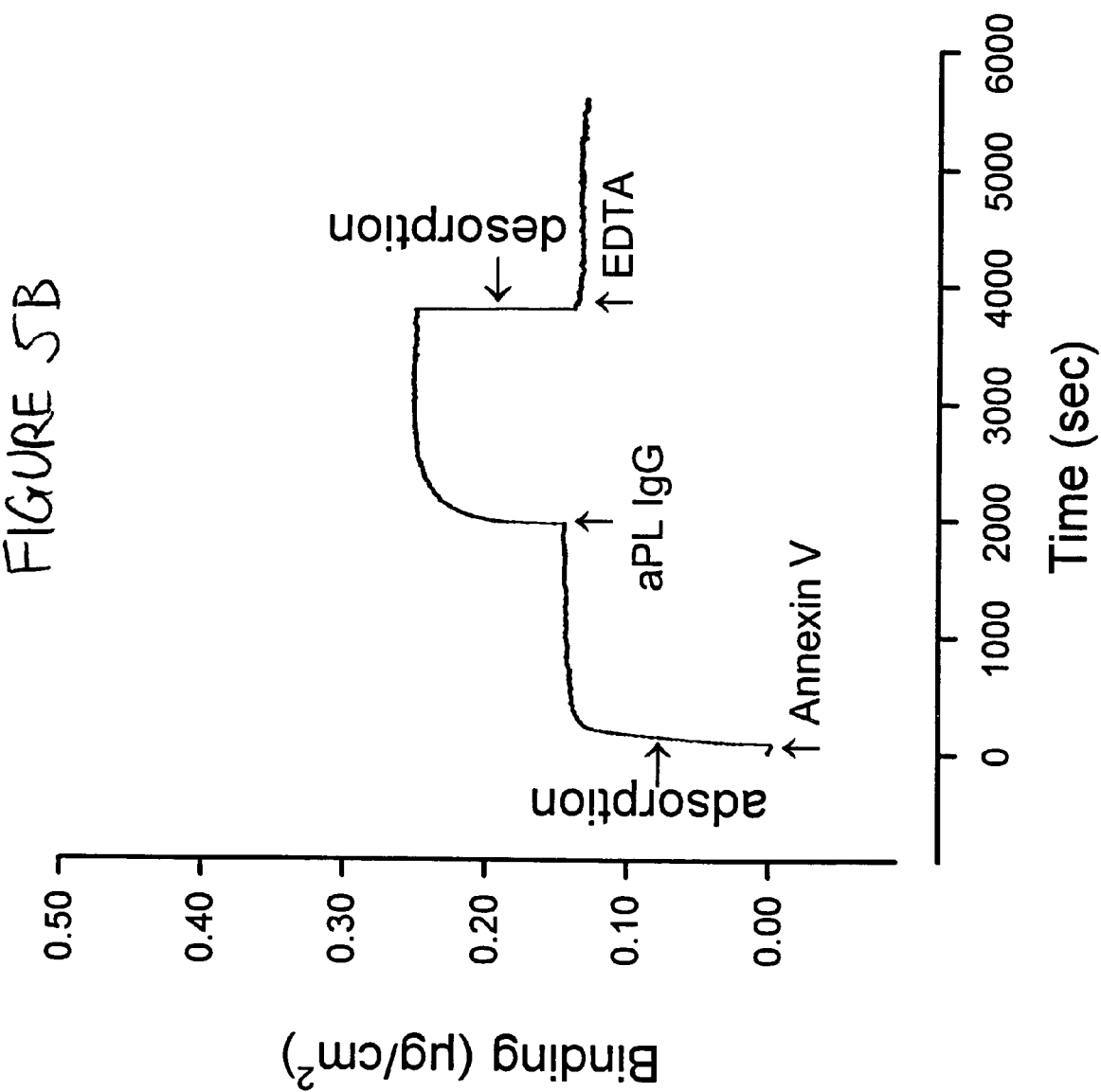
Figure 5C:
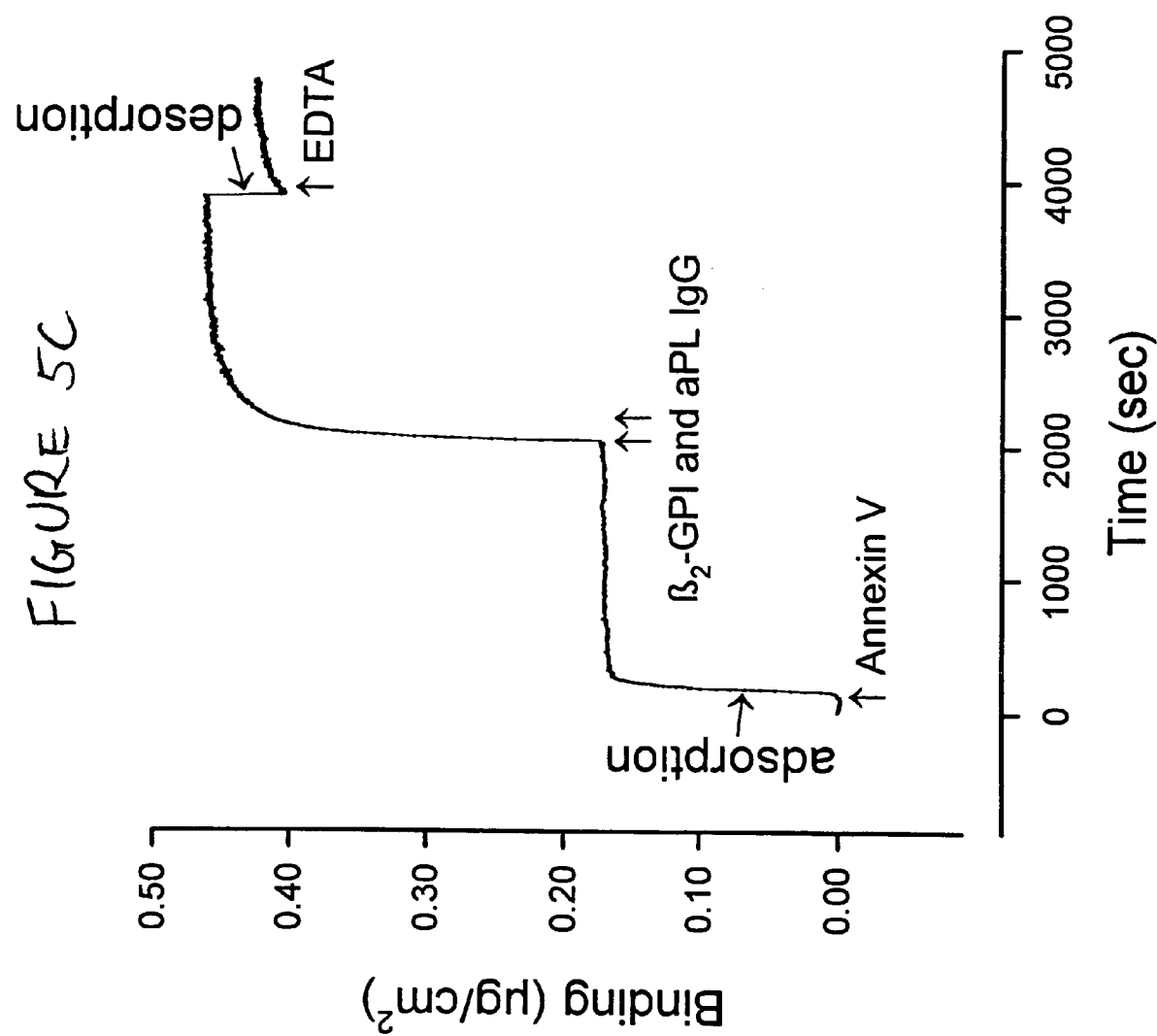
Figure 5D:
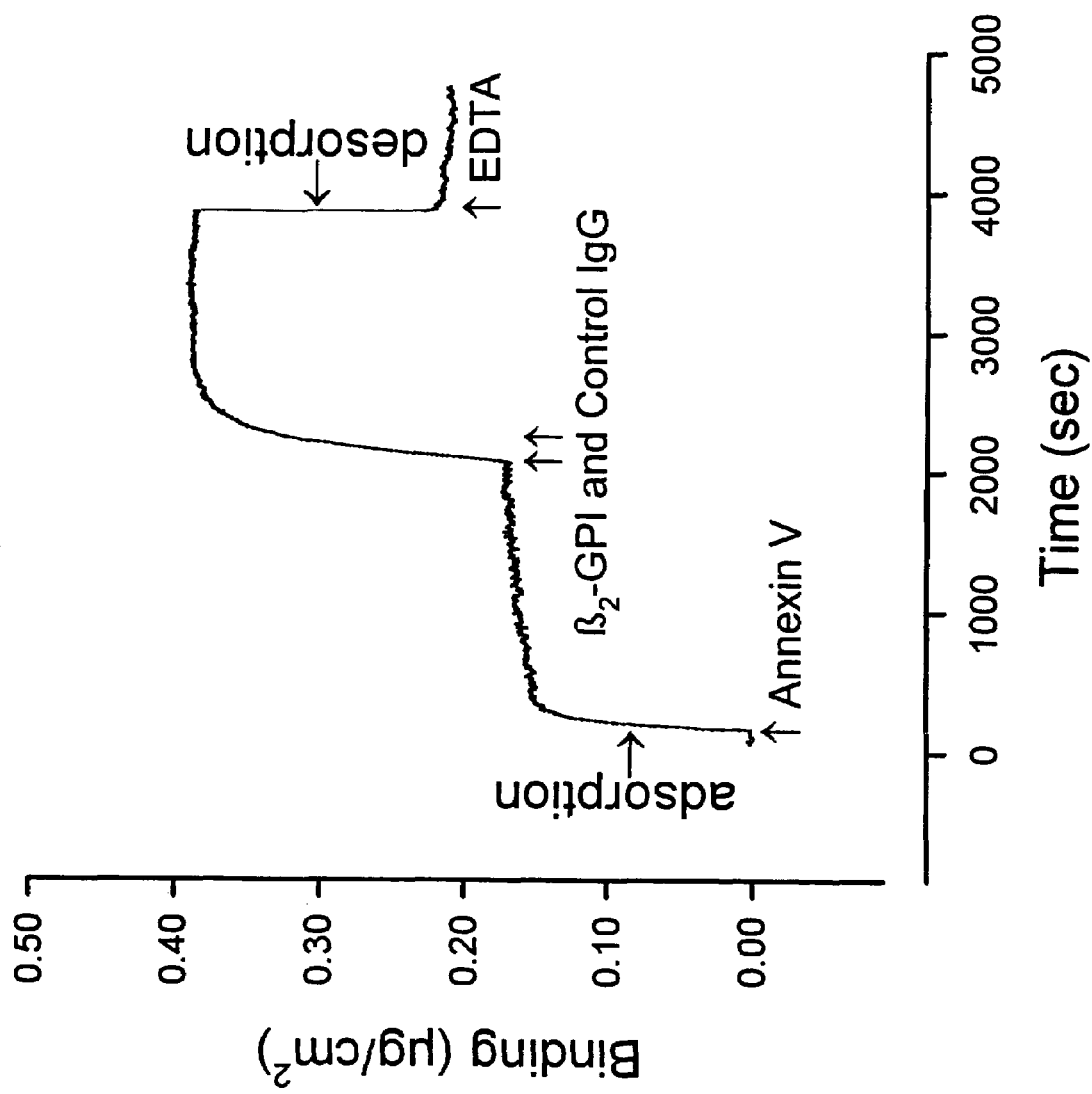
Figure 6:
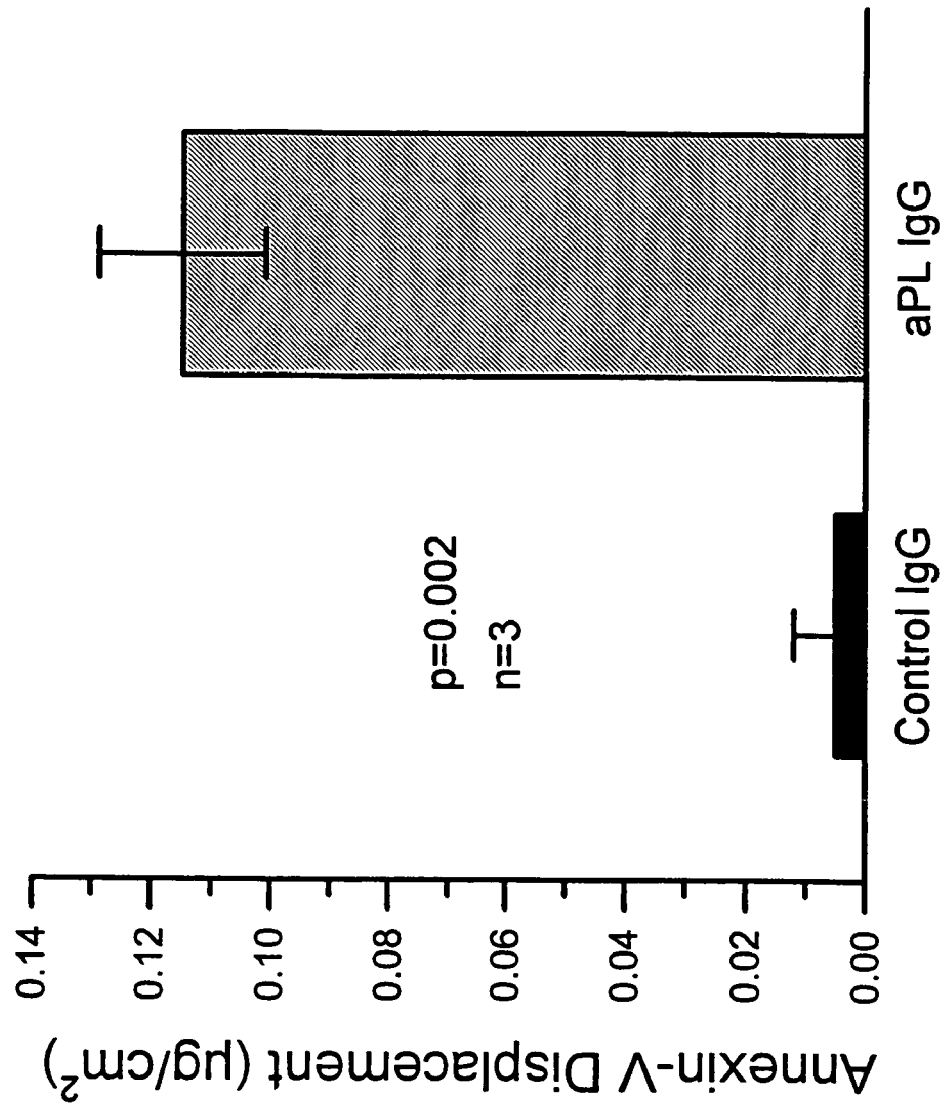
FIG. 6 shows quantitative displacement of annexin-V from the PS/PC phospholipid bilayers by aPL IgG preparations in the presence of $\beta_2$-GP I cofactor. The combination of aPL IgG with $\beta_2$-GP I significantly displace annexin-V from the bilayers as compared to control IgG with $\beta_2$-GP I. The mean (±SEM) quantity of annexin-V displaced by 3 different aPL syndrome patients' IgG fractions was 0.1150±014 $\mu g/cm^2$ as compared to no significant displacement by 3 different control IgG preparations (0.0050±0.007 $\mu g/cm^2$, p=0.002). These data demonstrate the displacement of annexin-V from the phospholipid bilayer surface by aPL IgG in the presence of $\beta_2$-GP I.

The quantity of annexin-V adsorbed to PS/PC (30%/70%) phospholipid bilayers on silicon slides was determined as described in Example 10, and the amount of annexin-V remaining on the phospholipid bilayers after addition of IgG preparations was determined by adding EDTA to desorb the residual annexin-V. All of the annexin-V which bound to the phospholipid surface was subsequently desorbed by addition of 6 mM EDTA (FIG. 5A). Since the adsorptions of IgGs and β$_2$-GP I were not affected by EDTA treatment, EDTA-induced desorption could be used to measure the amount of annexin-V remaining on the phospholipid surface after addition of aPL IgG antibodies. Measurement of the binding of 3 pairs of aPL IgG from aPL patients (Example 1) to the planar phospholipid bilayers of PS/PC-bound annexin-V showed that aPL IgG binding to the phospholipid bilayers, in the presence of (B$_2$-GP I cofactor, displaced 0.115±0.014 μg/cm$^2$ (mean±SEM) annexin-V from the phospholipid surface (FIGS. 5C & 6). In contrast, control IgG with the cofactor did not displace annexin-V (0.005±0.007 μg/cm$^2$, p=0.002) (FIGS. 5D & 6). Also, aPL IgG without the cofactor did not reduce the amount of adsorbed annexin-V (FIG. 5B), indicating that the cofactor was required when aPL IgGs were used. Immunoblotting of SDS solubilized slides after the EDTA desorption showed no residual annexin-V (data not shown).

EXAMPLE 17

Results of Annexin-V Binding to Phosphatidyl Serine-Coated Microtiter Plates

Figure 7:
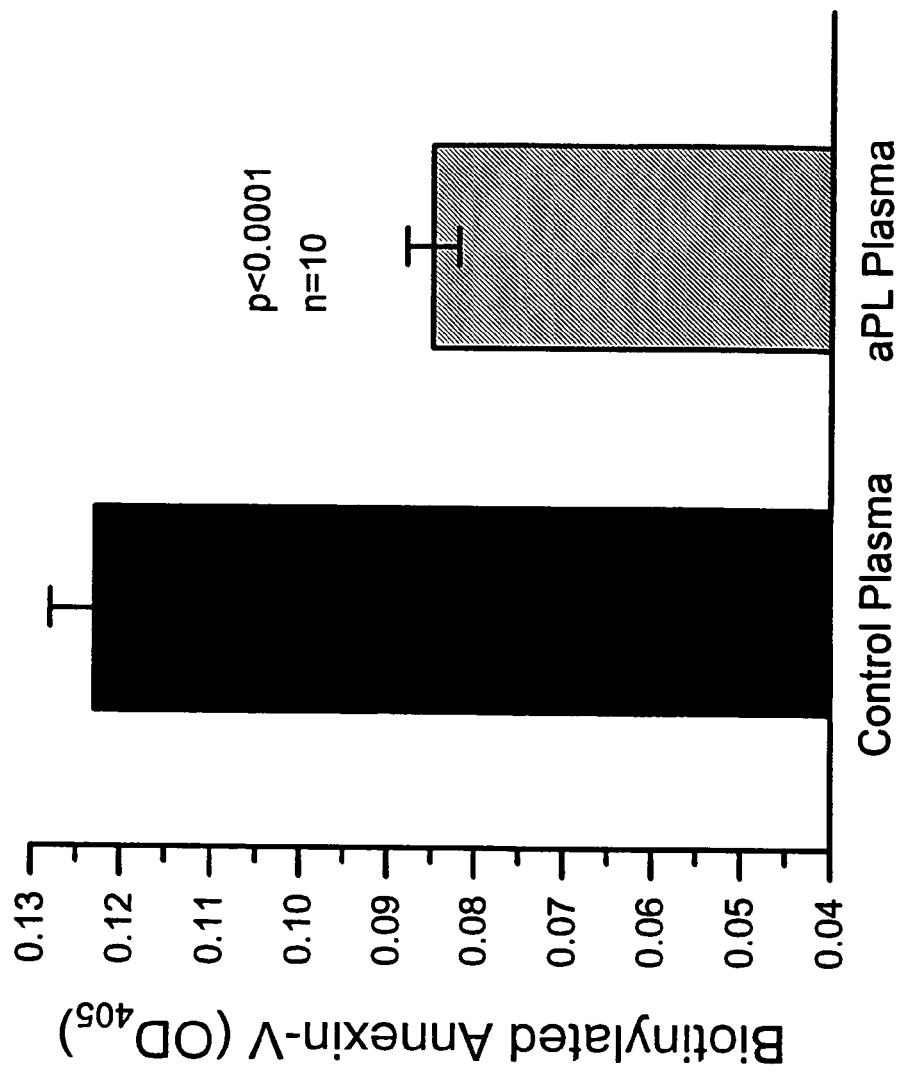
FIG. 7 shows annexin-V binding to microtiter plates coated with phosphatidyl serine (PS). PS-coated microtiter plate wells treated with aPL plasmas bound significantly less biotin-labeled annexin-V than PS-coated microtiter plate wells which had been treated with control plasmas. Annexin-V was detected by addition of phosphatase-labeled streptavidin followed by p-nitrophenyl phosphate substrate. The mean OD (±SEM) of the aPL plasma-treated wells was 0.085±0.003 and was 0.123±0.005 for the wells treated with control plasmas (n=1 0 for each group, p<0.0001).

PS-coated microtiter plates treated with aPL plasmas (Example 11) bound significantly less biotin-labeled annexin-V than PS-coated microtiter plates which had been treated with control plasmas (FIG. 7). The mean OD (±SEM) of the aPL plasma-treated wells was 0.085±0.003 compared to 0.123±0.005 for the wells treated with control plasmas (n=10 for each group, p<0.0001).

EXAMPLE 18

Results of Platelet Experiments

Figure 8:
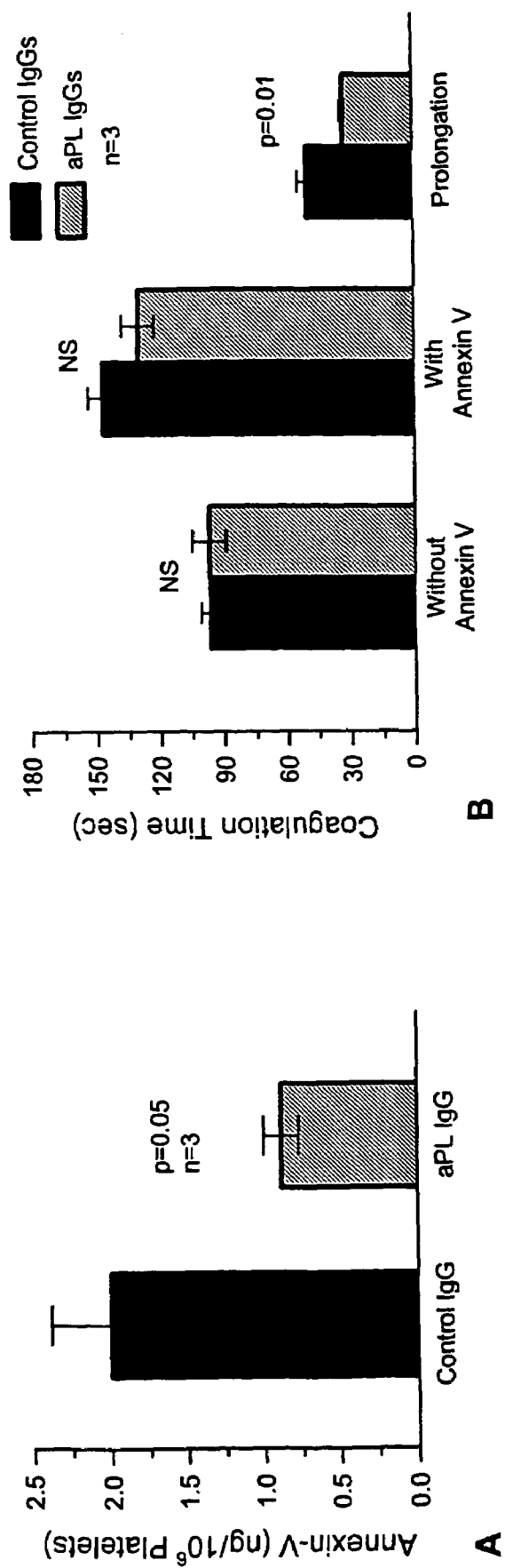
FIGS. 8A-B. The effects of aPL IgG on the quantity of platelet surface annexin-V and plasma coagulation.

The frozen thawed washed platelets (Example 12) which had been incubated with annexin-V after preincubation with aPL IgG preparations from the 3 different patients had significantly less annexin-V bound to their surfaces (mean±SEM-0.089±0.12 ng/10$^6$ platelets) than platelets which had been pre-exposed to control IgGs (2.01±0.38 ng/10$^6$ platelets, p=0.05, n=3) (FIG. 8A). Although annexin-V increased the coagulation times with both aPL and control IgG treatments, the protein had less of an anticoagulant effect with aPL IgG-treated platelets—i.e., there was significantly less prolongation with thawed washed platelets which had been pre-incubated with aPL IgG (mean±SEM-33.2±0.9 sec longer than coagulation time in absence of annexin-V) compared to control IgG (50.4±4.1 sec longer than coagulation time in absence of annexin-V, p=0.01, n=3) (FIG. 8B).

EXAMPLE 19 aPTT Reagent Results

Figure 9:
FIGS. 9A-B. The effects of aPL plasmas on annexin-V bound to aPTT reagent-phospholipid and plasma coagulation with this reagent.

In experiments utilizing aPTT reagent-phospholipid (Example 13), the aPTT reagent-phospholipid pre-exposed to aPL plasma was found to bind significantly less annexin-V (mean±SEM-318±28 ng/50 μl aliquot of reagent) than controls (656±80 ng/50 μl aliquot of reagent, p=0.01, n=4) (FIG. 9A). A two-stage test was designed to measure coagulation, in which aPTT reagent-phospholipid was first incubated with individual test plasma, washed, and for the second stage, exposed to a pooled normal plasma, which was then recalcified (to allow for caogulation to occur) in the presence and absence of added annexin-V. It was found that pre-exposure of aPTT reagent-phospholipid to plasmas from aPL syndrome patients significantly accelerated the coagulation of pooled normal plasma in the presence of annexin-V (mean±SEM:89.2±2.2 sec) as compared to control plasmas (mean±SEM-102.5±2.6 sec, p=0.001, n=10) (FIG. 9B). Also, there was a commensurate decrease in the annexin-V-induced anticoagulant effect, as assessed by prolongation of the coagulation time, of the aPL treated reagent as compared to the reagent which had been pre-incubated with control plasma (mean±SEM-13.6±1.8 sec for aPL patients and 23.1±0.8 sec for controls, p=0.0002) (FIG. 9B).

EXAMPLE 20

Prothrombin Time Reagent (tissue factor-phospholipid) Results

Figure 10:
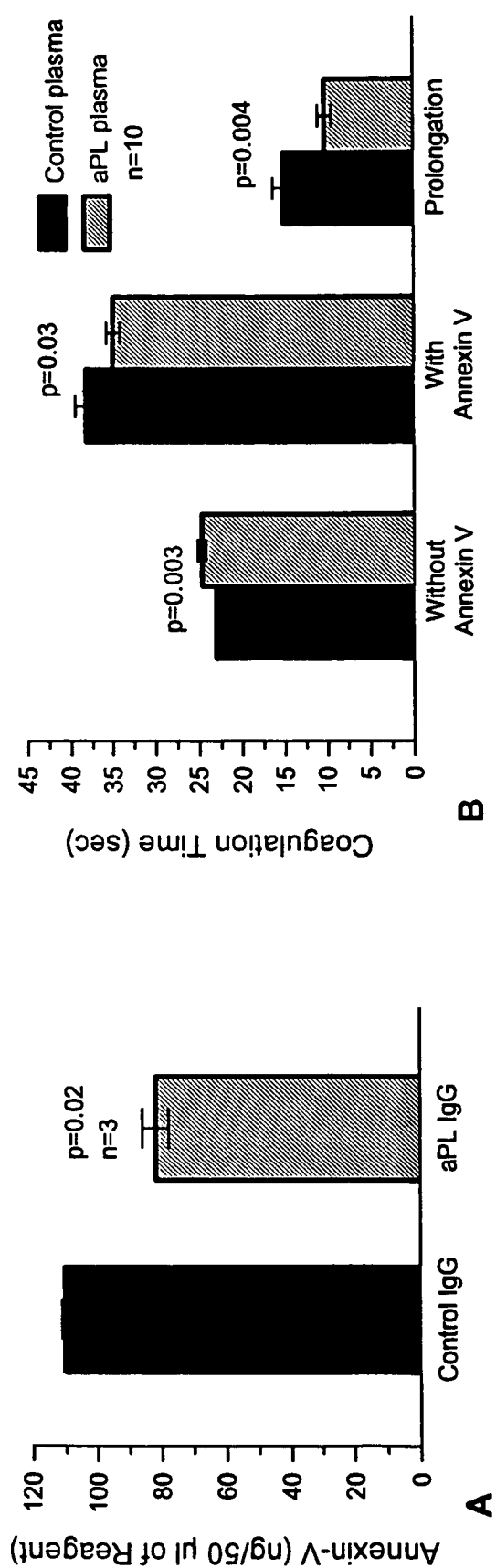
FIGS. 10A-B. The effects of aPL plasmas on annexin-V bound to prothrombin time reagent (tissue factor-phospholipid complex) and on plasma coagulation.

Similar experiments with tissue factor-phospholipid suspensions (PT reagent) (Example 14) also showed significantly less binding of annexin-V to PT reagent-phospholipid which had been pre-exposed to aPL IgG fractions (mean±SEM-82±4 ng/50 µl aliquot of reagent) than controls (110±1 ng/50 µl aliquot of reagent, p=0.02, n=3) (FIG. 10A). In the presence of annexin-V, PT reagent which had been pre-exposed to aPL plasmas accelerated the subsequent coagulation of pooled normal plasma (mean±SEM:35.0±0.8 sec) as compared to controls (38.3±1.2 sec, p=0.03, n=10) (FIG. 10B). There was a corresponding decrease in the annexin-V-induced anticoagulant effect with PT reagent which had been pre-incubated with aPL plasma (mean±SEM-0.10.3±0.8 sec) as compared to controls (15.2±1.2 sec, p=0.004). In contrast, in the absence of annexin-V, aPL-treated prothrombin time reagent caused a small but significant slowing of coagulation compared to prothrombin time reagent which had been pre-incubated with control plasma (mean±SEM:24.7±0.5 sec for aPL-treated reagent compared to 23.1±0.1 sec for controls, p=0.003) (FIG. 10B).

EXAMPLE 21

FITC-Annexin-V Binding to Phospholipid

Figure 11:
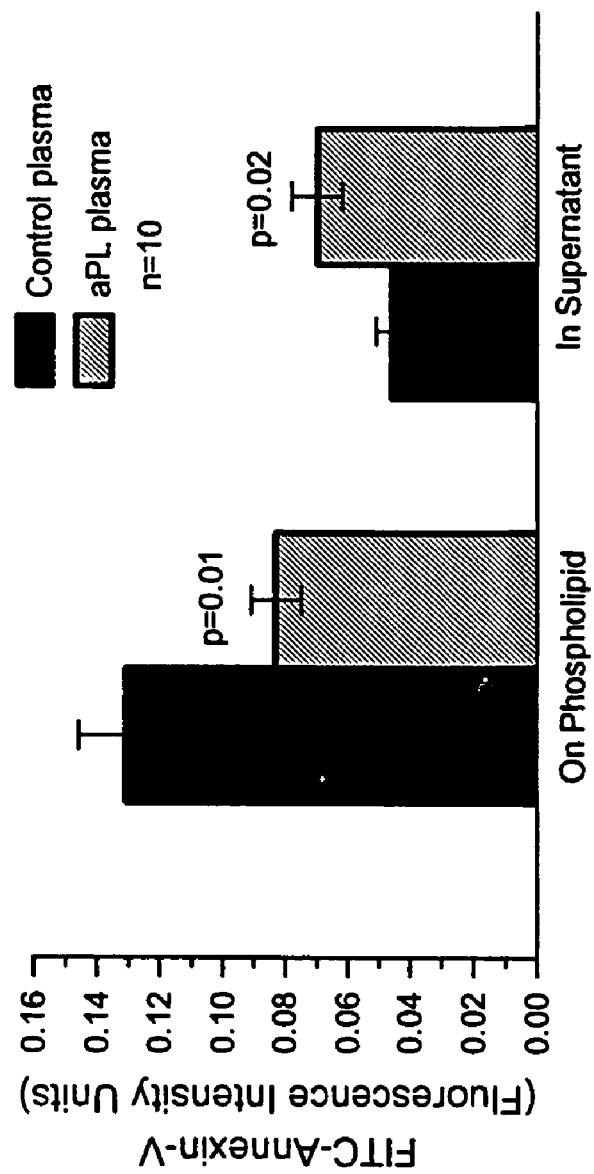
FIG. 11 shows the effects of aPL plasmas on the binding of FITC-annexin-V to aPTT reagentphospholipid. aPTT reagent was incubated with aPL and control plasmas (n=10 for each group), after which 1 μg/ml of FITC-annexin-V was added. Annexin-V bound to the aPTT reagent and in the fluid phase were quantified by spectrofluorimetry, as described in Methods. There was a significant decrease of the amount of annexin-V associated with the aPTT reagent which had been pre-incubated with aPL plasmas (mean±SEM-0.083±0.008 RFU/50 μl aliquot of reagent) compared to controls plasmas (0.131±0.015 RFU/50 μl aliquot of reagent, p=0.01). In contrast, there was a significant increase in the amount of labeled annexin-V remaining in the supernatant of aPTT reagent which had been preincubated with aPL plasmas (mean±SEM: 0.070±0.008 RFU/50 μl aliquot of reagent) as compared to control plasmas (0.046±0.005 RFU/50 μl aliquot of reagent, p=0.02).

Pre-exposure of aPTT reagent-phospholipid to aPL plasma was found to significantly reduce the amount of FITC-conjugated annexin-V (Example 15) which subsequently bound to the phospholipid (mean±SEM-0.083±0.008 RFU) as compared to control plasmas (0.131±0.015 RFU, p=0.01, n=10) (FIG. 11), and increase the amount of labeled annexin-V in the supernatant (mean±SEM-0.070±0.008 RFU for aPL exposed phospholipid and 0.046±0.005 RFU for control plasmas, p=0.02) (FIG. 11).

EXAMPLE 22

Effects of Antiphospholipid Antibodies and Annexin-V on Prothrombinase

The effect of annexin-V and aPL antibodies on phospholipid dependent prothrombinase (Factor Xa) was assayed using the following methodology. PS/PC (30%/70%, 5 mM, size 100 nanometers in diameter) vesical suspension was made by filtration through 100 nanometer membrane filters with an extruder, in a manner similar to that described in Example 10. Phospholipid bilayer coated slides were made as described in Example 10. The slides were transferred to an ellipsometer cuvette containing HEPES buffer (0.01 M HEPES, 0.14 M NaCl, pH 7.5) containing 1.25 mM $CaCl_2$, 0.02% BSA. Protein adsorption by the slides was observed with the ellipsometer. $\beta_2$-GP I (3 µg/ml) and aPL IgG (0.5 mg/ml) was then added to the cuvette, the proteins were absorbed at room temperature for 15 minutes. After adsorption had reached equilibrium, annexin-V was then added to a final concentration of 7 µg/ml. The adsorption reached equilibrium in 15-20 minutes. After which the slide was flushed with 10 ml of HEPES buffer containing 1.25 mM $CaCl_2$, 0.02% BSA, followed by 10 ml of HEPES buffer containing 5 mM $CaCl_2$, 0.1% BSA. Factor Xa (100 µM) and factor Va (1 nM) were then added. After adsorption for 10 minutes, prothrombin was added to a final concentration of 25 nM, sampling was done at intervals every 1 minute. 50 µl of sample was added into microtiter plate well which had been pre-filled with 100 µl of 36 mM EDTA in bicine buffer. 25 µl of the chromogenic substrate for thrombin, S2238 (Chromogenix, Sweden), was added to each well. Thrombin generation was monitored with a kinetic reader at wavelengths of 405 nm and 490 nm.

Annexin-V suppressed the phospholipid dependent activity of prothrombinase, and factor Xa, consequently the formation of thrombin. The addition of aPL antibodies and cofactor $\beta_2$-GP I to this reaction, resulted in the observation that annexin-V no longer suppressed the formation of thrombin. Whereas, control (non-aPL) antibodies/$\beta_2$-GP I had no effect on the formation of thrombin.

All references not previously specifically incorporated herein by reference are hereby incorporated herein.

I claim:
1. A method of diagnosing and/or monitoring antiphospholipid antibody syndrome in a patient comprising
   a. incubating in duplicate a phospholipid dependent coagulation test reagent with a sample of anticoagulated patient plasma,
   b. calcifying the plasma in one of the duplicate samples of step a in the presence of a standardized amount of annexin V and calcifying the plasma in the other sample in the absence of annexin V, and
   c. monitoring the time until clot formation occurs in each sample, and
   d. comparing the time until clot formation in the sample in the presence of annexin V to the sample in the absence of annexin V, wherein a reduced anticoagulant effect in the presence of annexin V indicates antiphospholipid antibody syndrome in the patient.
2. The method of claim 1, wherein the phospholipid dependent coagulation test reagent is selected from the group consisting of partial thromboplastin time reagent and prothrombin reagent.
3. The method of claim 1, wherein the patient has the antiphospholipid antibody syndrome.
4. The method of claim 1, wherein the plasma is citrated.
5. A method of diagnosing and/or monitoring antiphospholipid antibody syndrome in a patient comprising
   a. incubating in duplicate a phospholipid dependent coagulation test reagent with a sample of anticoagulated patient plasma or isolated patient IgG,
   b. removing unbound plasma or IgG from the coagulation test reagent,
   c. incubating the duplicate samples of step b with a sample of control plasma,
   d. calcifying the control plasma in one of the duplicate samples of step c in the presence of a standardized amount of annexin V and calcifying the control plasma in the other sample in the absence of annexin V and
   e. monitoring the time until clot formation occurs in each sample, and
   f. comparing the time until clot formation in the sample in the presence of annexin V to the sample in the absence of annexin V wherein a reduced anticoagulant effect in the presence of annexin V indicates antiphospholipid antibody syndrome disease in the patient.
6. The method of claim 5, wherein the phospholipid dependent coagulation test reagent is selected from the group consisting of partial thromboplastin time reagent and prothrombin reagent.
7. The method of claim 5, wherein the patient has the antiphospholipid antibody syndrome.
8. The method of claim 5, wherein the plasma is citrated.
9. The method of claim 5, wherein the control plasma is pooled normal plasma.

* * * * *

UNITED STATES PATENT AND TRADEMARK OFFICE
CERTIFICATE OF CORRECTION

| | | |
|---|---|---|
| PATENT NO. | : 7,252,959 B2 | Page 1 of 1 |
| APPLICATION NO. | : 11/028339 | |
| DATED | : August 7, 2007 | |
| INVENTOR(S) | : Jacob H. Rand | |

It is certified that error appears in the above-identified patent and that said Letters Patent is hereby corrected as shown below:

Please replace the paragraph beginning at Col. 1, line 14 and ending at Col. 1, line 16 with the following paragraph:

-- This invention was made with government support under NIH grant number AI 24671-07 awarded by the National Institutes of Health. The United States Government has certain rights in the invention. --

Signed and Sealed this

Twenty-second Day of September, 2009

David J. Kappos
*Director of the United States Patent and Trademark Office*